(12) United States Patent
Wada et al.

(10) Patent No.: US 8,614,076 B2
(45) Date of Patent: Dec. 24, 2013

(54) BACTERIUM CAPABLE OF PRODUCING LACTIC ACID, AND METHOD FOR PRODUCING LACTIC ACID

(75) Inventors: Mitsufumi Wada, Chiba (JP); Katsuyuki Takahashi, Singapore (SG); Takashi Morishige, Mobara (JP); Daisuke Miyazawa, Mobara (JP); Hitoshi Takahashi, Chiba (JP); Daisuke Mochizuki, Mobara (JP); Tadashi Araki, Chosei-gun (JP)

(73) Assignee: Mitsui Chemicals, Inc., Tokyo (JP)

( * ) Notice: Subject to any disclaimer, the term of this patent is extended or adjusted under 35 U.S.C. 154(b) by 244 days.

(21) Appl. No.: 13/063,923

(22) PCT Filed: Sep. 11, 2009

(86) PCT No.: PCT/JP2009/065956
§ 371 (c)(1),
(2), (4) Date: Mar. 14, 2011

(87) PCT Pub. No.: WO2010/032697
PCT Pub. Date: Mar. 25, 2010

(65) Prior Publication Data
US 2011/0171703 A1   Jul. 14, 2011

(30) Foreign Application Priority Data

Sep. 16, 2008 (JP) .................... 2008-237177
Feb. 13, 2009 (JP) .................... 2009-032042
Feb. 13, 2009 (JP) .................... 2009-032043

(51) Int. Cl.
*C12P 7/56* (2006.01)
(52) U.S. Cl.
USPC ........................................ 435/139
(58) Field of Classification Search
USPC ........................... 435/139, 252.33
See application file for complete search history.

(56) References Cited

U.S. PATENT DOCUMENTS

| | | | |
|---|---|---|---|
| 6,960,455 B2 | 11/2005 | Livshits et al. | |
| 2007/0065930 A1* | 3/2007 | Wada et al. | 435/139 |

FOREIGN PATENT DOCUMENTS

| | | |
|---|---|---|
| EP | 1 149 911 A2 | 10/2001 |
| EP | 1 669 460 | 6/2006 |
| JP | 63-233784 | 9/1988 |
| JP | 10-248574 | 9/1998 |
| JP | 2001-346578 | 12/2001 |
| JP | 2004-187643 | 7/2004 |
| WO | WO-2005/033324 A1 | 4/2005 |

OTHER PUBLICATIONS

Written Opinion PCT/JP2009/065956 (English Translation) filed Apr. 18, 2011.*
Aguilera, et al. "Dual Role of LldR in Regulation of the *lldPRD* Operon, Involved in $_L$-Lactate Metabolism in *Escherichia coli*", Journal of Bacteriology, Apr. 2008, vol. 190, No. 8, pp. 2997-3005.
Dong, et al. "Three Overlapping *lct* Genes Involved in L-Lactate Utilization by *Escherichia coli*", Journal of Bacteriology, Oct. 1993, vol. 175, No. 20, pp. 6671-6678.
Georgi, et al. "Regulation of $_L$-Lactate Utilization by the FadR-Type Regulator LldR of *Corynebacterium glutamicum*", Journal of Bacteriology, Feb. 2008, vol. 190, No. 3, pp. 963-971.
Grabar, et al. "Methylglyoxal bypass identified as source of chiral contamiantion in $_L$(+) and $_D$(−)-lactate fermentations by recombinant *Escherichia coli*", Biotechnol Lett, 2006, vol. 28, pp. 1527-1535.
International Search Report in PCT/JP2009/065956 dated Oct. 20, 2009.
Ishida, et al. "Efficient Production of $_L$-Lactic Acid by Metabolically Engineered *Saccharomyces cerevisiae* with a Genome-Integrated $_L$-Lactate Dehydrogenase Gene", Applied and Environmental Microbiology, Apr. 2005, vol. 71, No. 4, pp. 1964-1970.
Mochizuki, et al. "D-nyusan o Sentakuteki ni Koseisan suru Daichokin no Ikushu", Abstracts of the Annual Meeting of the Society for Biotechnology, Japan, Aug. 25, 2004, p. 253, 2K16-3.
Oikawa, et al. "Chemo-Enzymatic $_D$-Enantiomerization of $_{DL}$-Lactate", Biotechnology and Bioengineering, Apr. 2001, vol. 73, No. 1, pp. 80-82.
Orchard, et al. "Sequence similarities between the gene specifying 1-phosphofructokinase (*fruK*), genes specifying other kinases in *Escherichia coli* K12, and *lacC* of *Staphylococcus aureus*" Proc Biol Sci, 1990, vol. 242, pp. 87-90.
Shukla, et al. "Production of D(−)-lactate from sucrose and molasses" Biotechnolgy Letters, 2004, vol. 26, pp. 689-693.
Dien et al., "Recombinant *Escherichia coli* engineered for production of L-lactic acid from hexose and pentose sugars", Journal of Industrial Microbiology and Biotechnology, Basingstoke, GB, vol. 27, No. 4, pp. 259-264, Oct. 1, 2001, XP002419005.
European Search Report dated Nov. 15, 2012 issued in connection with European Application No. 09814542.8.

* cited by examiner

*Primary Examiner* — Tekchand Saidha
(74) *Attorney, Agent, or Firm* — Foley & Lardner LLP

(57) ABSTRACT

The present invention provides: a lactic acid-producing *Escherichia coli* including an enzymatic activity of at least one NAD-dependent lactate dehydrogenase and an enzymatic activity of at least one NAD-independent lactate oxidoreductase, both of which are enhanced so as to decompose one of D-lactic acid or L-lactic acid and to produce the other one of D-lactic acid or L-lactic acid; and a lactic acid production method using the lactic acid-producing *Escherichia coli*.

19 Claims, No Drawings

SEQUENCE LISTING

```
<160> NUMBER OF SEQ ID NOS: 69

<210> SEQ ID NO 1
<211> LENGTH: 18
<212> TYPE: DNA
<213> ORGANISM: Artificial
<220> FEATURE:
<223> OTHER INFORMATION: primer

<400> SEQUENCE: 1
caacaccaag ctttcgcg                                                  18

<210> SEQ ID NO 2
<211> LENGTH: 19
<212> TYPE: DNA
<213> ORGANISM: Artificial
<220> FEATURE:
<223> OTHER INFORMATION: primer

<400> SEQUENCE: 2
ttccactcct tgtggtggc                                                 19

<210> SEQ ID NO 3
<211> LENGTH: 26
<212> TYPE: DNA
<213> ORGANISM: Artificial
<220> FEATURE:
<223> OTHER INFORMATION: primer

<400> SEQUENCE: 3
aactgcagaa attacggatg gcagag                                         26

<210> SEQ ID NO 4
<211> LENGTH: 21
<212> TYPE: DNA
<213> ORGANISM: Artificial
<220> FEATURE:
<223> OTHER INFORMATION: primer

<400> SEQUENCE: 4
tgttctagaa agttctttga c                                              21

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
gcacgaaagc tttgattacg                                                20

<210> SEQ ID NO 6
<211> LENGTH: 30
<212> TYPE: DNA
<213> ORGANISM: Artificial
<220> FEATURE:
<223> OTHER INFORMATION: primer

<400> SEQUENCE: 6
```
ttattgcatg cttagatttg actgaaatcg                                          30

<210> SEQ ID NO 7
<211> LENGTH: 30
<212> TYPE: DNA
<213> ORGANISM: Artificial
<220> FEATURE:
<223> OTHER INFORMATION: primer

<400> SEQUENCE: 7
ttattgcatg cttatttact gcgtacttcg                                          30

<210> SEQ ID NO 8
<211> LENGTH: 21
<212> TYPE: DNA
<213> ORGANISM: Artificial
<220> FEATURE:
<223> OTHER INFORMATION: primer

<400> SEQUENCE: 8
aaggcctacg aaaagctgca g                                                   21

<210> SEQ ID NO 9
<211> LENGTH: 30
<212> TYPE: DNA
<213> ORGANISM: Artificial
<220> FEATURE:
<223> OTHER INFORMATION: primer

<400> SEQUENCE: 9
aaaggtacca gaataccttc tgctttgccc                                          30

<210> SEQ ID NO 10
<211> LENGTH: 30
<212> TYPE: DNA
<213> ORGANISM: Artificial
<220> FEATURE:
<223> OTHER INFORMATION: primer

<400> SEQUENCE: 10
aaaggatccc ctaaactcct tattatattg                                          30

<210> SEQ ID NO 11
<211> LENGTH: 30
<212> TYPE: DNA
<213> ORGANISM: Artificial
<220> FEATURE:
<223> OTHER INFORMATION: primer

<400> SEQUENCE: 11
aaaggatcca aaccggagca cagactccgg                                          30

<210> SEQ ID NO 12
<211> LENGTH: 30
<212> TYPE: DNA
<213> ORGANISM: Artificial
<220> FEATURE:
<223> OTHER INFORMATION: primer

<400> SEQUENCE: 12
aaatctagaa tcagatcatc gtcgccttac                                          30

<210> SEQ ID NO 13
<211> LENGTH: 30
<212> TYPE: DNA
<213> ORGANISM: Artificial
<220> FEATURE:

<223> OTHER INFORMATION: primer

<400> SEQUENCE: 13
ttttgagctc gatcaggatt gcgttggtgg                             30

<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
cgaacagtaa tcgtacaggg                                        20

<210> SEQ ID NO 15
<211> LENGTH: 35
<212> TYPE: DNA
<213> ORGANISM: Artificial
<220> FEATURE:
<223> OTHER INFORMATION: primer

<400> SEQUENCE: 15
tacgattact gttcggcatc gaccgaatac ccgag                       35

<210> SEQ ID NO 16
<211> LENGTH: 30
<212> TYPE: DNA
<213> ORGANISM: Artificial
<220> FEATURE:
<223> OTHER INFORMATION: primer

<400> SEQUENCE: 16
tttttctaga cctggcacgc ctctcttctc                             30

<210> SEQ ID NO 17
<211> LENGTH: 30
<212> TYPE: DNA
<213> ORGANISM: Artificial
<220> FEATURE:
<223> OTHER INFORMATION: primer

<400> SEQUENCE: 17
aacgaattct cgcaatgatt gacacgattc                             30

<210> SEQ ID NO 18
<211> LENGTH: 32
<212> TYPE: DNA
<213> ORGANISM: Artificial
<220> FEATURE:
<223> OTHER INFORMATION: primer

<400> SEQUENCE: 18
acagaattcg ctatttgtta gtgaataaaa gg                          32

<210> SEQ ID NO 19
<211> LENGTH: 28
<212> TYPE: DNA
<213> ORGANISM: Artificial
<220> FEATURE:
<223> OTHER INFORMATION: primer

<400> SEQUENCE: 19
ggaattccgg agaaagtctt atgaaact                               28

<210> SEQ ID NO 20

```
<211> LENGTH: 29
<212> TYPE: DNA
<213> ORGANISM: Artificial
<220> FEATURE:
<223> OTHER INFORMATION: primer

<400> SEQUENCE: 20
cccaagcttt taaaccagtt cgttcgggc                                        29

<210> SEQ ID NO 21
<211> LENGTH: 26
<212> TYPE: DNA
<213> ORGANISM: Artificial
<220> FEATURE:
<223> OTHER INFORMATION: primer

<400> SEQUENCE: 21
aaggtaccac cagagcgttc tcaagc                                           26

<210> SEQ ID NO 22
<211> LENGTH: 30
<212> TYPE: DNA
<213> ORGANISM: Artificial
<220> FEATURE:
<223> OTHER INFORMATION: primer

<400> SEQUENCE: 22
gctctagatt ctccagtgat gttgaatcac                                       30

<210> SEQ ID NO 23
<211> LENGTH: 28
<212> TYPE: DNA
<213> ORGANISM: Artificial
<220> FEATURE:
<223> OTHER INFORMATION: primer

<400> SEQUENCE: 23
ggtctagagc aatgattcac acgattcg                                         28

<210> SEQ ID NO 24
<211> LENGTH: 28
<212> TYPE: DNA
<213> ORGANISM: Artificial
<220> FEATURE:
<223> OTHER INFORMATION: primer

<400> SEQUENCE: 24
aactgcaggt tcgttctcat acacgtcc                                         28

<210> SEQ ID NO 25
<211> LENGTH: 38
<212> TYPE: DNA
<213> ORGANISM: Artificial
<220> FEATURE:
<223> OTHER INFORMATION: primer

<400> SEQUENCE: 25
gggaattcga catcattcgc tcgtctattc tttcgata                              38

<210> SEQ ID NO 26
<211> LENGTH: 33
<212> TYPE: DNA
<213> ORGANISM: Artificial
<220> FEATURE:
<223> OTHER INFORMATION: primer

<400> SEQUENCE: 26
```

```
gggtaccttn aggaatcatc cacgttaaga cat                              33
```

<210> SEQ ID NO 27
<211> LENGTH: 50
<212> TYPE: DNA
<213> ORGANISM: Artificial
<220> FEATURE:
<223> OTHER INFORMATION: primer

<400> SEQUENCE: 27

```
atggtacccg gagaaagtct tatgattatt ccgcagcca gcgattatcg            50
```

<210> SEQ ID NO 28
<211> LENGTH: 34
<212> TYPE: DNA
<213> ORGANISM: Artificial
<220> FEATURE:
<223> OTHER INFORMATION: primer

<400> SEQUENCE: 28

```
gatgtcgacc tatgccgcat tccctttcgc catg                            34
```

<210> SEQ ID NO 29
<211> LENGTH: 29
<212> TYPE: DNA
<213> ORGANISM: Artificial
<220> FEATURE:
<223> OTHER INFORMATION: primer

<400> SEQUENCE: 29

```
tactgcagat ctcaataacc gctatctgg                                  29
```

<210> SEQ ID NO 30
<211> LENGTH: 28
<212> TYPE: DNA
<213> ORGANISM: Artificial
<220> FEATURE:
<223> OTHER INFORMATION: primer

<400> SEQUENCE: 30

```
gctctagata gccattgtac tggtatgg                                   28
```

<210> SEQ ID NO 31
<211> LENGTH: 27
<212> TYPE: DNA
<213> ORGANISM: Artificial
<220> FEATURE:
<223> OTHER INFORMATION: primer

<400> SEQUENCE: 31

```
tatctagatg ctcagccgta gctaagc                                    27
```

<210> SEQ ID NO 32
<211> LENGTH: 27
<212> TYPE: DNA
<213> ORGANISM: Artificial
<220> FEATURE:
<223> OTHER INFORMATION: primer

<400> SEQUENCE: 32

```
cgaattcatc catctgacat tcgctgg                                    27
```

<210> SEQ ID NO 33
<211> LENGTH: 33
<212> TYPE: DNA
<213> ORGANISM: Artificial
<220> FEATURE:

<223> OTHER INFORMATION: primer

<400> SEQUENCE: 33
cgagctacat atgcaatgat tgacacgatt ccg                       33

<210> SEQ ID NO 34
<211> LENGTH: 29
<212> TYPE: DNA
<213> ORGANISM: Artificial
<220> FEATURE:
<223> OTHER INFORMATION: primer

<400> SEQUENCE: 34
tctagagcta tttgttagtg aataaaagg                            29

<210> SEQ ID NO 35
<211> LENGTH: 43
<212> TYPE: DNA
<213> ORGANISM: Artificial
<220> FEATURE:
<223> OTHER INFORMATION: primer

<400> SEQUENCE: 35
gatctagacg gagaaagtct tatgacgcaa tctcgattgc atg            43

<210> SEQ ID NO 36
<211> LENGTH: 29
<212> TYPE: DNA
<213> ORGANISM: Artificial
<220> FEATURE:
<223> OTHER INFORMATION: primer

<400> SEQUENCE: 36
atggtacctt aacccagttg ccagagtgc                            29

<210> SEQ ID NO 37
<211> LENGTH: 52
<212> TYPE: DNA
<213> ORGANISM: Artificial
<220> FEATURE:
<223> OTHER INFORMATION: primer

<400> SEQUENCE: 37
attctagacg gagaaagtct tatggaaaaa acatatcaag caggtacaaa tg  52

<210> SEQ ID NO 38
<211> LENGTH: 37
<212> TYPE: DNA
<213> ORGANISM: Artificial
<220> FEATURE:
<223> OTHER INFORMATION: primer

<400> SEQUENCE: 38
caggtacctt aaataaaacg attctcacgc aattta                    37

<210> SEQ ID NO 39
<211> LENGTH: 50
<212> TYPE: DNA
<213> ORGANISM: Artificial
<220> FEATURE:
<223> OTHER INFORMATION: primer

<400> SEQUENCE: 39
attctagacg gagaaagtct tatgattatt tccgcagcca gcgattatcg     50

<210> SEQ ID NO 40

<211> LENGTH: 34
<212> TYPE: DNA
<213> ORGANISM: Artificial
<220> FEATURE:
<223> OTHER INFORMATION: primer

<400> SEQUENCE: 40
gatggtaccc tatgccgcat tccctttcgc catg                                34

<210> SEQ ID NO 41
<211> LENGTH: 1191
<212> TYPE: DNA
<213> ORGANISM: Artificial
<220> FEATURE:
<221> NAME/KEY: CDS

<400> SEQUENCE: 41
atgattattt ccgcagccag cgattatcgc gctgcagcgc aacgcattct gccgccgttc      60
ctgttccact atatggatgg tggtgcatat tctgaataca cgctgcgccg caacgtggaa     120
gatttgtcag aagtggcgct gcgccagcgt attctgaaaa acatgtccga cttaagcctg     180
gaaacgacgc tgtttaatga aaattgtcg atgccggtgg cactggctcc ggtgggtttg     240
tgtggcatgt atgcgcgtcg tggcgaagtt caggcagcca aagcggcgga cgcgcatggt     300
attccgttta ctctctcgac ggtttccgtt tgcccgattg aagaagtcgc gccagccatc     360
aagcgcccaa tgtggttcca gctttatgta ctgcgcgatc gcggctttat gcgtaacgcg     420
ctggagcgag caaaagcagc gggttgttcg acgctggttt tcaccgtgga tatgccgaca     480
ccgggcgcac gctaccgtga tgcgcattca ggtatgagcg gcccgaacgc ggcaatgcgc     540
cgctacttgc aagcggtgac acatccgcaa tgggcgtggg atgtgggcct gaacggtcgt     600
ccacatgatt taggtaatat ctcagcttat ctcggcaaac cgaccggact ggaagattac     660
atcggctggc tggggaataa cttcgatccg tccatctcat ggaaagacct tgaatggatc     720
cgcgatttct gggatggccc gatggtgatc aaagggatcc tcgatccgga agatgcgcgc     780
gatgcagtac gttttggtgc tgatggaatt gtggtttcta accacggtgg ccgccagctg     840
gacggtgtac tctcttccgc ccgtgcactg cctgctattg cagatgcggt gaaaggtgat     900
atagccattc tggcggatag cggaattcgt aacgggcttg atgtcgtgcg tatgattgcg     960
ctcggtgccg acaccgtact gctgggtcgt gctttcttgt atgcgctggc aacagcgggc    1020
caggcgggtg tagctaacct gctaaatctg atcgaaaaag atgaaagt ggcgatgacg     1080 ctgactggcg cgaaatcgat cagcgaaatt acgcaagatt cgctggtgca ggggctgggt    1140
aaagagttgc ctgcggcact ggctcccatg gcgaaaggga atgcggcata g             1191

<210> SEQ ID NO 42
<211> LENGTH: 51
<212> TYPE: DNA
<213> ORGANISM: Artificial
<220> FEATURE:
<223> OTHER INFORMATION: primer

<400> SEQUENCE: 42
atcgtcgacc ggagaaagtc ttatgattat ttccgcagcc agcgattatc g             51

<210> SEQ ID NO 43
<211> LENGTH: 53
<212> TYPE: DNA
<213> ORGANISM: Artificial
<220> FEATURE:
<223> OTHER INFORMATION: primer

```
<400> SEQUENCE: 43
aattctagac ggagaaagtc ttatgcatct atcatctaca gatgtaaact tta        53

<210> SEQ ID NO 44
<211> LENGTH: 38
<212> TYPE: DNA
<213> ORGANISM: Artificial
<220> FEATURE:
<223> OTHER INFORMATION: primer

<400> SEQUENCE: 44
acaggtacct tagtcaatca atgaggtatg tttgattt                          38

<210> SEQ ID NO 45
<211> LENGTH: 52
<212> TYPE: DNA
<213> ORGANISM: Artificial
<220> FEATURE:
<223> OTHER INFORMATION: primer

<400> SEQUENCE: 45
atggtacccg gagaaagtct tatggaaaaa acatatcaag caggtacaaa tg         52

<210> SEQ ID NO 46
<211> LENGTH: 37
<212> TYPE: DNA
<213> ORGANISM: Artificial
<220> FEATURE:
<223> OTHER INFORMATION: primer

<400> SEQUENCE: 46
cagtcgactt aaataaaacg attctcacgc aatttta                          37

<210> SEQ ID NO 47
<211> LENGTH: 53
<212> TYPE: DNA
<213> ORGANISM: Artificial
<220> FEATURE:
<223> OTHER INFORMATION: primer

<400> SEQUENCE: 47
aatggtaccc ggagaaagtc ttatgcatct atcatctaca gatgtaaact tta        53

<210> SEQ ID NO 48
<211> LENGTH: 38
<212> TYPE: DNA
<213> ORGANISM: Artificial
<220> FEATURE:
<223> OTHER INFORMATION: primer

<400> SEQUENCE: 48
acagtcgact tagtcaatca atgaggtatg tttgattt                          38

<210> SEQ ID NO 49
<211> LENGTH: 43
<212> TYPE: DNA
<213> ORGANISM: Artificial
<220> FEATURE:
<223> OTHER INFORMATION: primer

<400> SEQUENCE: 49
aatctagacg gagaaagtct tatggcggaa actaccgtta agc                   43

<210> SEQ ID NO 50
<211> LENGTH: 28
```

```
<212> TYPE: DNA
<213> ORGANISM: Artificial
<220> FEATURE:
<223> OTHER INFORMATION: primer

<400> SEQUENCE: 50
ctgtctagat cagaagccga actgggcg                                              28

<210> SEQ ID NO 51
<211> LENGTH: 28
<212> TYPE: DNA
<213> ORGANISM: Artificial
<220> FEATURE:
<223> OTHER INFORMATION: primer

<400> SEQUENCE: 51
gctctagagc attcctgaca gcagaagc                                              28

<210> SEQ ID NO 52
<211> LENGTH: 28
<212> TYPE: DNA
<213> ORGANISM: Artificial
<220> FEATURE:
<223> OTHER INFORMATION: primer

<400> SEQUENCE: 52
aactgcagtc ggcgtgtagt agtgaacc                                              28

<210> SEQ ID NO 53
<211> LENGTH: 28
<212> TYPE: DNA
<213> ORGANISM: Artificial
<220> FEATURE:
<223> OTHER INFORMATION: primer

<400> SEQUENCE: 53
ggaagcttca aattggcgtc tctgatct                                              28

<210> SEQ ID NO 54
<211> LENGTH: 35
<212> TYPE: DNA
<213> ORGANISM: Artificial
<220> FEATURE:
<223> OTHER INFORMATION: primer

<400> SEQUENCE: 54
aaacccgggc catccatata gtggaacagg aacgg                                      35

<210> SEQ ID NO 55
<211> LENGTH: 28
<212> TYPE: DNA
<213> ORGANISM: Artificial
<220> FEATURE:
<223> OTHER INFORMATION: primer

<400> SEQUENCE: 55
gggctcgagt ggcgatgacg ctgactgg                                              28

<210> SEQ ID NO 56
<211> LENGTH: 38
<212> TYPE: DNA
<213> ORGANISM: Artificial
<220> FEATURE:
<223> OTHER INFORMATION: primer
```

```
<400> SEQUENCE: 56
cgtctagaac gggtaaatct ggtggtgacc gtcacccg                           38

<210> SEQ ID NO 57
<211> LENGTH: 43
<212> TYPE: DNA
<213> ORGANISM: Artificial
<220> FEATURE:
<223> OTHER INFORMATION: primer

<400> SEQUENCE: 57
aagaattccg gagaaagtct tatggcggaa actaccgtta agc                    43

<210> SEQ ID NO 58
<211> LENGTH: 29
<212> TYPE: DNA
<213> ORGANISM: Artificial
<220> FEATURE:
<223> OTHER INFORMATION: primer

<400> SEQUENCE: 58
ggtctagagc aatgattgac acgattccg                                    29

<210> SEQ ID NO 59
<211> LENGTH: 31
<212> TYPE: DNA
<213> ORGANISM: Artificial
<220> FEATURE:
<223> OTHER INFORMATION: primer

<400> SEQUENCE: 59
cggaattccg ctatttgtta gtgaataaaa g                                 31

<210> SEQ ID NO 60
<211> LENGTH: 29
<212> TYPE: DNA
<213> ORGANISM: Artificial
<220> FEATURE:
<223> OTHER INFORMATION: primer

<400> SEQUENCE: 60
cgggtacctt cgccaccaca aggagtgga                                    29

<210> SEQ ID NO 61
<211> LENGTH: 35
<212> TYPE: DNA
<213> ORGANISM: Artificial
<220> FEATURE:
<223> OTHER INFORMATION: primer

<400> SEQUENCE: 61
ggtctagagt cgacttactc cacttcctgc cagtt                             35

<210> SEQ ID NO 62
<211> LENGTH: 39
<212> TYPE: DNA
<213> ORGANISM: Artificial
<220> FEATURE:
<223> OTHER INFORMATION: primer

<400> SEQUENCE: 62
gcggtacccg gagaaagtct tatgacgcaa ccaggacag                         39

<210> SEQ ID NO 63
<211> LENGTH: 37
<212> TYPE: DNA
```

```
<213> ORGANISM: Artificial
<220> FEATURE:
<223> OTHER INFORMATION: primer

<400> SEQUENCE: 63
tgggtacctt aggcccagtc cttgtgcggc gacgtgc                              37

<210> SEQ ID NO 64
<211> LENGTH: 38
<212> TYPE: DNA
<213> ORGANISM: Artificial
<220> FEATURE:
<223> OTHER INFORMATION: primer

<400> SEQUENCE: 64
gcggtacccg gagaaagtct tatggtgcag cttccttc                             38

<210> SEQ ID NO 65
<211> LENGTH: 38
<212> TYPE: DNA
<213> ORGANISM: Artificial
<220> FEATURE:
<223> OTHER INFORMATION: primer

<400> SEQUENCE: 65
gtggtaccct atctccaata agcggccttg ctggtatg                             38

<210> SEQ ID NO 66
<211> LENGTH: 44
<212> TYPE: DNA
<213> ORGANISM: Artificial
<220> FEATURE:
<223> OTHER INFORMATION: primer

<400> SEQUENCE: 66
aacccgggcg gagaaagtct tatgactgat ggacttccca ccgc                      44

<210> SEQ ID NO 67
<211> LENGTH: 48
<212> TYPE: DNA
<213> ORGANISM: Artificial
<220> FEATURE:
<223> OTHER INFORMATION: primer

<400> SEQUENCE: 67
atcccgggtc actctgcggg cgatgtgggc agcaccttgc ccggattc                  48

<210> SEQ ID NO 68
<211> LENGTH: 45
<212> TYPE: DNA
<213> ORGANISM: Artificial
<220> FEATURE:
<223> OTHER INFORMATION: primer

<400> SEQUENCE: 68
ttggtaccgg agaaagtctt atgaccgatg tacttcccac cgcac                     45

<210> SEQ ID NO 69
<211> LENGTH: 47
<212> TYPE: DNA
<213> ORGANISM: Artificial
<220> FEATURE:
<223> OTHER INFORMATION: primer

<400> SEQUENCE: 69
ttggtaccta ggcgggcggc aacaccttgc caggattcaa gatccca                   47
```

BACTERIUM CAPABLE OF PRODUCING LACTIC ACID, AND METHOD FOR PRODUCING LACTIC ACID

TECHNICAL FIELD

The present invention relates to a lactic acid-producing bacterium and a method of producing lactic acid.

RELATED ART

Lactic acid includes L-lactic acid and D-lactic acid. L-lactic acid is a raw material for industrially produced polylactic acid. D-lactic acid has also attracted increasing attention in recent years as a raw material for polymers or as an intermediate for agrochemicals and medicines. However, lactic acid as a raw material is required to have high optical purity in any of the uses described above.

In nature, there are microorganisms that produce lactic acid with high efficiency, and lactic acid production methods using the microorganisms are employed in some cases. However, by-products such as compounds including acetic acid, ethanol, acetoin, and pyruvic acid are also produced with the methods, which may lead to deterioration in the quality of lactic acid that is the final product. Further, a decrease in optical purity due to incorporation of optical isomers may raise a serious problem.

In order to avoid such decrease in the purity of lactic acid, a method whereby production of a by-product of interest is specifically inhibit by disrupting a specific gene of a microorganism by using a genetic recombination technique has been developed in recent years. In particular, lactic acid production techniques with high optical purity are under development using *Escherichia coli*, yeast, and the like of which abundant genome information is available and which has sufficient successful records as hosts for genetic engineering, rather than applications to microorganisms intrinsically capable of producing lactic acid with high yield such as lactic acid bacteria and filamentous bacteria.

For example, Biotechnol Lett. 2006 October; 28(19): 1527-1535 (document by Grabar, et al.) describes that L-lactic acid with high optical purity can successfully be produced by culturing an *Escherichia coli* in a synthetic medium composed of minerals including 1 mM betaine, wherein the *Escherichia coli* produces L-lactate dehydrogenase derived from *Pediococcus acidilactici*, and, in the *Escherichia coli*, a D-lactate dehydrogenase gene (ldhA), which is a gene involved in the metabolic pathway of from pyruvic acid to D-lactic acid in *Escherichia coli*, and an msgA gene, which is a gene involved in the metabolic pathway of from methylglyoxal to D-lactic acid in *Escherichia coli*, are disrupted.

According to this document, it has been demonstrated that when an *Escherichia coli* in which an msgA gene is not disrupted is used in the presence of betaine, the optical purity that can be achieved even with disruption of a D-lactate dehydrogenase gene (ldhA) is only about 96% e.e. even in the absence of incorporation of D-lactic acid into a raw material. This is because D-lactic acid derived from methylglyoxal is biosynthesized by the *Escherichia coli*.

It has also been demonstrated that even though the *Escherichia coli* described in the document has a FAD-dependent D-lactate dehydrogenase gene (dld) for decomposition of D-lactic acid, the optical purity that can be achieved in the presence of betaine is about from 95% to 96% if the msgA gene is not disrupted. That is, it has been demonstrated that expression of the innate dld gene of an *Escherichia coli* alone is incapable of sufficiently decomposing even a slight amount of D-lactic acid synthesized by the *Escherichia coli*, which leads to inability to achieve high optical purity. Further, it has also been demonstrated that the production rate of the desired lactic acid is decreased to about a half in a medium that does not contain betaine, although lactic acid with high optical purity of 99% or more can be produced from a raw material not containing D-lactic acid.

Based on the above, it has been demonstrated that it is difficult to simultaneously achieve high production efficiency and high optical purity of L-lactic acid when disruption of the msgA gene and addition of betaine are not conducted.

Further, the document relates to production of L-lactic acid with high optical purity achieved by inhibiting the production of D-lactic acid by *Escherichia coli* and using a medium that does not contain D-lactic acid. However, the document does not describe any method for increasing optical purity when D-lactic acid is included in medium components.

Japanese Patent Application Laid-Open (JP-A) No. 2004-187643 discloses a method of lowering lactate racemase activity in order to achieve high optical purity. Although this method is effective when a lactic acid-producing bacterium synthesizes DL-lactic acid, this method is not effective when the medium includes DL-lactic acid.

Further, Biotech. Bioeng., Vol. 73(1), pp 80-82 (2001) discloses a method whereby a D-lactic acid solution is obtained from a mixture solution of DL-lactic acid by using L-lactate dehydrogenase. However, the experiment described in this report is carried out at a small scale of 1 mL and at a low lactic acid concentration of about 10 mM. Therefore, this method cannot be considered to be effective for industrial production using lactic acid-producing bacteria, in which the lactic acid concentration is generally 1000 mM or higher.

According to the pamphlet of WO2005/033324, D-lactic acid with high optical purity was successfully produced from a medium containing corn steep liquor, by using an *Escherichia coli* of which dld gene is disrupted. Corn steep liquor includes DL-lactic acid, and D-lactic acid with high optical purity was successfully produced by the *Escherichia coli* of which dld gene is disrupted, because decomposition of D-lactic acid under microaerobic conditions is suppressed, and D-lactic acid is produced while L-lactic acid is decomposed. This document demonstrates that aeration affects the metabolism rate of sugars, the decomposition rate of optical isomers, and the production rate of impurities, and that excessive aeration decreases the production rate of lactic acid due to a decrease in the metabolism rate of sugars. Therefore, it is also demonstrated that, when lactic acid production is desired, there is an upper limit of the aeration rate, and an optimum aeration rate needs to be determined. That is, the amount of oxygen that can be supplied for L-lactic acid decomposition, which is an aerobic metabolic reaction, should be an amount that does not decrease the production rate of D-lactic acid.

A higher lactic acid production rate is industrially preferable. An optical isomer that causes a decrease in optical purity is preferably decomposed as rapidly as possible. Enzymes that decompose L-lactic acid or D-lactic acid into pyruvic acid convert lactic acid into pyruvic acid by using a coenzyme such as flavin mononucleotide (FMN) or flavin adenine dinucleotide (FAD) or by directly using oxygen. Even in the case of enzymes using a coenzyme, respiration—i.e. utilization of oxygen—is efficient for the regeneration of the coenzyme. Consequently, the enzymatic activity of each enzyme is limited by the amount of oxygen that can be supplied.

When the amount of oxygen supplied is increased, although a lactic acid that causes a decrease in optical purity is rapidly decomposed, the metabolism rate of sugars decreases, and the production rate of the desired lactic acid sharply decreases. For these reasons, it was extremely difficult to increase the decomposition rate of a lactic acid derived from extracellular raw materials irrespective of oxygen amount, and thereby improve the optical purity of a desired lactic acid within a shorter time.

SUMMARY OF INVENTION

Technical Problem

Therefore, it is an object of the present invention to provide a lactic acid-producing *Escherichia coli* and a method of producing lactic acid, with which lactic acid with high optical purity is produced within a shorter time.

Technical Solution

The present invention includes the following.

[1] A lactic acid-producing *Escherichia coli* comprising an enzymatic activity of at least one NAD-dependent lactate dehydrogenase and an enzymatic activity of at least one NAD-independent lactate oxidoreductase, both of which are enhanced so as to decompose one of D-lactic acid or L-lactic acid and to produce the other one of D-lactic acid or L-lactic acid.

[2] The lactic acid-producing *Escherichia coli* according to [1], wherein the enhancement of the NAD-dependent lactate dehydrogenase activity causes production of one of D-lactic acid or L-lactic acid from pyruvic acid, and the enhancement of the NAD-independent lactate oxidoreductase activity causes decomposition of the other one of D-lactic acid or L-lactic acid as a substrate.

[3] The lactic acid-producing *Escherichia coli* according to [1] or [2], wherein the enhancement of the NAD-dependent lactate dehydrogenase activity is enhancement of LdhA activity, and provides capability of producing D-lactic acid.

[4] The lactic acid-producing *Escherichia coli* according to [3], wherein the enhancement of the NAD-independent lactate oxidoreductase activity is enhancement of LldD activity, enhancement of L-lactate oxidase activity, inactivation or attenuation of LldR, or a combination of one or more thereof, and provides capability of producing D-lactic acid.

[5] The lactic acid-producing *Escherichia coli* according to [4], wherein the L-lactate oxidase is at least one of Lox or LctO.

[6] The lactic acid-producing *Escherichia coli* according to [4] or [5], wherein the enhancement of the NAD-independent lactate oxidoreductase activity is by a mutated lldD gene having a silent mutation at position 33 in ORF of a LldD-encoding gene.

[7] The lactic acid-producing *Escherichia coli* according to [6], wherein the mutated lldD is represented by a base sequence of SEQ ID NO: 41.

[8] The lactic acid-producing *Escherichia coli* according to any one of [3] to [7], wherein at least one selected from the group consisting of Dld activity and Pfl activity is inactivated or attenuated.

[9] The lactic acid-producing *Escherichia coli* according to [1] or [2], wherein the enhancement of the NAD-dependent lactate dehydrogenase activity is enhancement of NAD-dependent L-lactate dehydrogenase activity, and provides capability of producing L-lactic acid.

[10] The lactic acid-producing *Escherichia coli* according to [9], wherein the enhancement of the NAD-independent lactate oxidoreductase activity is enhancement of activity of Dld, and provides capability of producing L-lactic acid.

[11] The lactic acid-producing *Escherichia coli* according to [9] or [10], wherein the L-lactate dehydrogenase is derived from a bacterium of the genus *Bifidobacterium*.

[12] The lactic acid-producing *Escherichia coli* according to [10] or [11], wherein the Dld comprises a Lact deh memb domain.

[13] The lactic acid-producing *Escherichia coli* according to any one of [10] to [12], wherein the Dld is derived from at least one selected from the group consisting of *Escherichia coli*, *Zymomonas* and *Corynebacterium*.

[14] The lactic acid-producing *Escherichia coli* according to any one of [9] to [13], wherein at least one of LdhA activity, LldD activity or Pfl activity is inactivated or attenuated.

[15] The lactic acid-producing *Escherichia coli* according to any one of [1] to [14], wherein at least one selected from the group consisting of Mdh activity and AspA activity is inactivated or attenuated.

[16] The lactic acid-producing *Escherichia coli* according to any one of [1] to [15], wherein at least one selected from the group consisting of sucrose non-PTS genes and FruK is enhanced.

[17] The lactic acid-producing *Escherichia coli* according to any one of [1] to [16], wherein FruR activity is inactivated or attenuated.

[18] A method of producing lactic acid, the method comprising:
producing lactic acid by using the lactic acid-producing *Escherichia coli* of any one of [1] to [17].

[19] A method of producing D-lactic acid, the method comprising: producing D-lactic acid by using the lactic acid-producing *Escherichia coli* of any one of [3] to [8].

[20] A method of producing L-lactic acid, the method comprising: producing L-lactic acid by using the lactic acid-producing *Escherichia coli* of any one of [9] to [14].

EMBODIMENTS FOR CARRYING OUT INVENTION

The lactic acid-producing *Escherichia coli* according to the invention is a lactic acid-producing *Escherichia coli* comprising an enzymatic activity of at least one NAD-dependent lactate dehydrogenase and an enzymatic activity of at least one NAD-independent lactate oxidoreductase, both of which are enhanced so as to decompose one of D-lactic acid or L-lactic acid and to produce the other one of D-lactic acid or L-lactic acid.

The *Escherichia coli* according to the invention has both an enhanced enzymatic activity of at least one NAD-dependent lactate dehydrogenase and an enhanced enzymatic activity of at least one NAD-independent lactate oxidoreductase in a lactic acid metabolism system, and is capable of decomposing one of D-lactic acid or L-lactic acid in order to produce the other one of D-lactic acid or L-lactic acid. Therefore, with the *Escherichia coli* according to the invention, production of one of D-lactic acid or L-lactic acid and rapid decomposition of an optical isomer decreasing the optical purity can proceed simutaneously.

As a result, it is possible to provide a lactic acid-producing *Escherichia coli* and a lactic acid production method, with which lactic acid with high optical purity is produced within a shorter time.

The "enhancement" of an enzymatic activity in the invention encompasses, in addition to introduction of a gene encoding the enzyme of interest into a host bacterium from the outside of the bacterium to the inside of the bacterium, enhancement of the enzymatic activity that results from enhancement of the promoter activity for the enzyme gene that the host bacterium posseses on its genome, strong expression of the enzyme gene by replacement with another promoter, or attenuation or inactivation of a repressor activity against the enzyme gene.

The "attenuation" of an enzymatic activity in the invention refers to a state in which the activity of the enzyme of interest is significantly decreased by genetic recombination of a gene encoding the enzyme of interest, as compared to a state before the recombination treatment is conducted.

The "inactivation" of an enzymatic activity in the invention refers to a state in which the activity of the enzyme of interest measured is below the detection limit regardless of the measurement system from among existing measurement systems.

Further, the "host" in the invention means an *Escherichia coli* that becomes the lactic acid-producing *Escherichia coli* according to the invention as a result of introduction of one or more genes from outside the bacterial cell.

Each numerical range described in the present specification represents a range including the indicated values as the minimum value and the maximum value, respectively.

The invention is described in detail below.

In order to produce one of D-lactic acid or L-lactic acid, both an enzymatic activity of at least one NAD-dependent lactate dehydrogenase and an enzymatic activity of at least one NAD-independent lactate oxidoreductase are enhanced in the lactic acid-producing *Escherichia coli* according to the invention, such that the other one of D-lactic acid or L-lactic acid is decomposed into the one of D-lactic acid or L-lactic acid. Specifically, it is preferable that the enhancement of the NAD-dependent lactate dehydrogenase activity causes production of one of D-lactic acid or L-lactic acid from pyruvic acid, and that the NAD-independent lactate oxidoreductase decomposes the other one of D-lactic acid or L-lactic acid as a substrate. As a result, production of D-lactic acid or L-lactic acid from pyruvic acid is ensured, and decomposition of the other one of D-lactic acid or L-lactic acid is promoted, and, therefore, lactic acid with high optical purity is more specifically obtained with high efficiency.

The "NAD-dependent lactate dehydrogenase" refers to a lactate dehydrogenase of which coenzyme is NAD and that is classified to enzyme number 1.1.1.27 or enzyme number 1.1.1.28 according to the enzyme committee report of the International Union of Biochemistry (I.U.B.). In the lactic acid metabolism system, this enzyme performs an oxidoreduction reaction between L-lactic acid or D-lactic acid and pyruvic acid using NAD as a coenzyme. This enzyme has a function of performing an oxidoreduction reaction in accordance with the amount of the substrate, the amount of NAD, and the like. Enhancement of the activity of a NAD-dependent lactate dehydrogenase that produces D-lactic acid or L-lactic acid from pyruvic acid is preferable from the viewpoint of producing lactic acid with high optical purity.

As the gene capable of introducing a NAD-dependent lactate dehydrogenase enzymatic activity into a host bacterium, a DNA having the base sequence of a gene that encodes a NAD-dependent lactate dehydrogenase and that is obtained from an organism possessing this enzyme, or a synthetic DNA sequence synthesized based on a known base sequence of the gene, may be used. Preferable examples thereof include those derived from bacteria belonging to the genus *Escherichia*, bacteria belonging to the genus *Pseudomonas*, bacteria belonging to the genus *Aerobacter*, bacteria belonging to the genus *Clostridium*, and bacteria belonging to the genus *Bifidobacterium*, particularly those derived from bacteria belonging to the genus *Escherichia* and bacteria belonging to the genus *Bifidobacterium*. Examples thereof include a DNA having the base sequence of a gene derived from an *Escherichia coli* MG1655 strain and a DNA having the base sequence of a gene derived from a *Bifidobacterium longum*.

The "NAD-independent lactate oxidoreductase" in the invention refers to a lactate dehydrogenase of which coenzyme is a factor other than NAD, or a lactate oxidase that oxidizes lactic acid by directly using oxygen. This enzyme is an enzyme that performs an oxidoreduction reaction between L-lactic acid or D-lactic acid and pyruvic acid in a lactic acid metabolism system, by using FAD, FMN, or the like as a coenzyme, or by directly using oxygen. This enzyme has a function of performing an oxidoreduction reaction in accordance with the amount of substrate, the amount of a coenzyme, and the like. In the invention, this enzyme is preferably an enzyme that enhances a function capable of decomposing one of D-lactic acid or L-lactic acid as a substrate up into pyruvic acid.

As the gene capable of introducing NAD-independent lactate oxidoreductase enzymatic activity into a host bacterium, a DNA having the base sequence of a gene that encodes NAD-independent lactate oxidoreductase and that is obtained from an organism possessing this enzyme, or a synthetic DNA sequence synthesized based on a known base sequence of the gene, may be used. Preferable examples thereof include those derived from bacteria belonging to the genus *Escherichia*, bacteria belonging to the genus *Pseudomonas*, bacteria belonging to the genus *Aerobacter*, bacteria belonging to the genus *Clostridium*, bacteria belonging to the genus *Enterococcus*, bacteria belonging to the genus *Streptococcus*, bacteria belonging to the genus *Pediococcus*, bacteria belonging to the genus *Lactococcus*, bacteria belonging to the genus *Aerococcus*, bacteria belonging to the genus *Corynebacterium*, and bacteria belonging to the genus *Zymomonas*, particularly those derived from bacteria belonging to the genus *Escherichia*, bacteria belonging to the genus *Enterococcus*, bacteria belonging to the genus *Corynebacterium*, and bacteria belonging to the genus *Zymomonas*. Examples thereof include a DNA having the base sequence of a gene derived from an *Escherichia coli* MG1655 strain, a DNA having the base sequence of a gene derived from an *Enterococcus* sp. ATCC9625 strain, a DNA having the base sequence of a gene derived from a *Corynebacterium glutamicum* NBRC 12168 strain, and a DNA having the base sequence of a gene derived from a *Zymomonas mobilis* ATCC31821 strain.

When a NAD-independent lactate oxidoreductase and a NAD-dependent lactate dehydrogenase are used in combination and the activity of each of the enzymes is enhanced, one of the optical isomers is produced while the other one of the optical isomers, which decreases optical purity, is decomposed, whereby lactic acid can be produced rapidly with high optical purity.

In the lactic acid-producing *Escherichia coli* according to the invention, the genes to be enhanced may be any genes that contribute to the enhancement of the respective enzymatic activities described above. Enhancement with the genes described below is preferable from the viewpoints of the optical purity and efficiency of production of D-lactic acid or L-lactic acid.

A D-lactic acid-producing bacterium that produces D-lactic acid and an L-lactic acid-producing bacterium that produces L-lactic acid are separately described below.

<D-lactic Acid-Producing Bacterium>

In the D-lactic acid-producing bacterium according to the invention, LdhA activity is preferably enhanced as the enhancement of the activity of an NAD-dependent lactate dehydrogenase.

The D-lactate dehydrogenase (LdhA) which is used as the NAD-dependent lactate dehydrogenase in the invention and of which the activity is to be enhanced refers to an enzyme that produces D-lactic acid and NAD from pyruvic acid and NADH. Both of an LdhA enzyme that produces L-lactic acid and an LdhA enzyme that produces D-lactic acid are known in general. However, in the invention, only an LdhA enzyme that produces D-lactic acid is denoted as "LdhA", in order to avoid confusion in the invention.

The ldhA gene may be a DNA having the base sequence of the gene that is obtained from an organism having an activity of this enzyme, or a synthetic DNA sequence synthesized based on a known base sequence of the gene.

Preferable examples of the ldhA gene include those derived from the bacteria described in the above explanation of the NAD-dependent lactate dehydrogenase, and specifically examples include a gene acquired by Bunch, et al. (Microbiology 1,43 (Pt 1), pp. 187-195 (1997)), or a gene having the sequence contained in the below-described DNA fragment that is amplified by PCR using the genomic DNA of *Escherichia coli* as a template and using SEQ ID NO: 19 and SEQ ID NO: 20.

A method including integrating a gene encoding LdhA into an expression plasmid so as to be linked to a gene promoter that controls expression of a protein involved in a glycolytic system, a nucleic acid biosynthesis system, or an amino acid biosynthesis system, and introducing the expression plasmid into a desired bacterium, is an effective measure to enhance LdhA activity in the invention. In this case, the gene promoter that controls the expression of a protein involved in the glycolytic system, the nucleic acid biosynthesis system, or the amino acid biosynthesis system refers to a strong promoter that constantly functions in a bacterium, preferably in *Escherichia coli*, and that is less susceptible to expression suppression even in the presence of glucose. Specific examples thereof include a promoter of glyceraldehyde-3-phosphate dehydrogenase and a promoter of serine hydroxymethyltransferase. When the *Escherichia coli* thus obtained is used in the production of D-lactic acid under aerobic conditions, the accumulation amount of D-lactic acid is increased, and the optical purity of D-lactic acid can be improved, compared to a case in which the expression of ldhA is not enhanced.

In the D-lactic acid-producing bacterium according to the invention, the enhancement of NAD-independent lactate oxidoreductase activity is preferably enhancement of LldD activity, enhancement of L-lactate oxidase activity, inactivation or attenuation of LldR, or a combination of one or more thereof.

Therefore, L-lactic acid can be efficiently decomposed into pyruvic acid, and optical purity can be rapidly increased when producing D-lactic acid.

The NAD-independent L-lactate dehydrogenase (LldD) which is used as the NAD-independent lactate oxidoreductase in the invention and of which the activity is to be enhanced as refers to an enzyme that is classified to enzyme number 1.1.2.3 according to the enzyme committee report of the International Union of Biochemistry (I.U.B.), and that produces pyruvic acid and FMNH from L-lactic acid and FMN. The lldD gene may be a DNA having the base sequence of the gene that is obtained from an organism having the activity of this enzyme, or a synthetic DNA sequence synthesized based on a known base sequence of the gene.

Preferable examples thereof include those derived from bacteria belonging to the genus *Escherichia*, bacteria belonging to the genus *Pseudomonas*, bacteria belonging to the genus *Shigella*, bacteria belonging to the genus *Citrobacter*, and bacteria belonging to the genus *Salmonella*, particularly those derived from bacteria belonging to the genus *Escherichia*. Examples thereof include a DNA having the base sequence of a gene derived from an *Escherichia coli* MG1655 strain.

From the viewpoint of achieving more rapid decomposition of L-lactic acid, the LldD is preferably a LldD expressed by a mutant lldD gene having a silent mutation at the position 33 of the sequence of encoding the ORF of the lldD gene, and is more preferably a mutant lldD (C33T mutant lldD) (SEQ ID NO: 41) of which the base at the position 33 has been changed from C to T. A high-activity *Escherichia coli* variant can be easily obtained by introducing the C33T mutant lldD gene into an *Escherichia coli* by a known genetic recombination technique. The use of this high-activity variant enables decomposition of L-lactic acid at higher rates and improvement in the optical purity of D-lactic acid.

The L-lactate oxidase which is used as the NAD-independent lactate dehydrogenase and of which the activity is to be enhanced refers to an enzyme that is classified to enzyme number 1.13.12.—according to the enzyme committee report of the International Union of Biochemistry (I.U.B.), and that produces pyruvic acid and hydrogen peroxide in the presence of L-lactic acid and oxygen. Here, lox or lctO, which is a gene for this enzyme, may be a DNA having the base sequence of the gene that is obtained from an organism having the activity of this enzyme, or a synthetic DNA sequence synthesized based on a known base sequence of the gene.

Preferable examples thereof include those derived from bacteria belonging to the genus *Enterococcus*, bacteria belonging to the genus *Streptococcus*, bacteria belonging to the genus *Pediococcus*, bacteria belonging to the genus *Lactococcus*, and bacteria belonging to the genus *Aerococcus*. Among them, those isolated from *Enterococcus* sp. ATCC9625 and *Lactococcus lactis* ATCC 19435 are particularly preferable.

A method including integrating a gene encoding LldD or L-lactate oxidase into an expression plasmid so as to be linked to a gene promoter that controls expression of a protein involved in a glycolytic system, a nucleic acid biosynthesis system, or an amino acid biosynthesis system, and introducing the expression evector into a desired *Escherichia coli*, is an effective measure to enhance the activity of LldD or L-lactate oxidase in the invention. In this case, the gene promoter that controls the expression of a protein involved in the glycolytic system, the nucleic acid biosynthesis system, or the amino acid biosynthesis system refers to a strong promoter that constantly functions in a bacterium, preferably in *Escherichia coli*, and that is less susceptible to expression suppression even in the presence of glucose. Specific examples thereof include a promoter of glyceraldehyde-3-phosphate dehydrogenase and a promoter of serine hydroxymethyltransferase. When the *Escherichia coli* thus obtained is used in the production of D-lactic acid under aerobic conditions, the accumulation amount of D-lactic acid is increased, and the optical purity of D-lactic acid can be improved, as compared to a case in which the expression of LldD or L-lactate oxidase is not enhanced.

Each of LldD and L-lactate oxidase may have a known sequence thereof without any modification, or may alternatively be a mutant that does not deteriorate its enzymatic activity. Examples of the mutation include addition, deletion, conversion, or the like of amino acid(s). The mutant that does not deteriorate the enzymatic activity can be obtained according to a method known in the art.

LldR that is to be inactivated or attenuated in order to enhance the activity of the NAD-independent lactate dehydrogenase is a control factor that inhibits the transcription of the L-lactate dehydrogenase (LldD). The attenuation or inactivation of LldR activity prevents LldD activity from being inhibited, or effectively enhances LldD activity.

In the D-lactic acid-producing bacterium according to the invention, it is preferable that at least one selected from the group consisting of Dld activity and Pfl activity is inactivated or attenuated.

The "FAD-dependent D-lactate dehydrogenase (Dld)" in the invention is a generic name for enzymes that catalyze a reaction of generating pyruvic acid from D-lactic acid in the presence of oxidized flavin adenine dinucleotide serving as a coenzyme. Decomposition of D-lactic acid, which is a product, can be inhibited by inactivating or attenuating Dld activity.

The pyruvate formate lyase (Pfl) in the invention is an enzyme classified to enzyme number 2.3.1.54 according to the enzyme committee report of the International Union of Biochemistry (I.U.B.), and is also called "formate acetyl transferase". The "pyruvate formate lyase (Pfl)" is a generic name for enzymes that reversibly catalyze a reaction of generating formic acid from pyruvic acid. Decomposition of pyruvic acid, which is a raw material for the production of D-lactic acid, can be inhibited by inactivating or attenuating Pfl activity.

An example of a microorganism in which LdhA activity is enhanced while either of Dld activity or Pfl activity or both are inactivated or attenuated in the invention is an *Escherichia coli* MT-10994 (FERM BP-10058) strain described in WO2005/033324.

In addition to the above, it is preferable that at least one selected from the group consisting of the activity of Mdh and the activity of AspA in the D-lactic acid-producing bacterium according to the invention is inactivated or attenuated, from the viewpoint of suppressing the amount of by-products produced.

The malate dehydrogenase (Mdh) in the invention is classified to enzyme number 1.1.1.37 according to the enzyme committee report of the International Union of Biochemistry (I.U.B.), and is a generic name for enzymes that reversibly catalyze a reaction of generating oxaloacetic acid from malic acid in the presence of oxidized nicotinamide adenine dinucleotide serving as a coenzyme. Therefore, production of succinic acid as a by-product can be inhibited by inactivating or attenuating the activity of Mdh.

The aspartate ammonia lyase (AspA) in the invention is an enzyme classified to enzyme number 4.3.1.1 according to the enzyme committee report of the International Union of Biochemistry (I.U.B.), and is called "aspartase". The "aspartate ammonia lyase (AspA)" is a generic name for enzymes that reversibly catalyze a reaction of generating fumaric acid from L-aspartic acid. Therefore, production of fumaric acid as a by-product can be inhibited by inactivating or attenuating the activity of AspA.

The D-lactic acid-producing bacterium according to the invention can produce D-lactic acid using a sugar such as glucose as a raw material. In the D-lactic acid-producing bacterium according to the invention, at least one selected from the group consisting of a sucrose non-PTS gene group and FruK may be enhanced in order to enable the production of D-lactic acid using another sugar as a raw material, and it is preferable that both the sucrose non-PTS gene group and FruK are enhanced, and it is more preferable that only cscA from among the sucrose non-PTS gene group and FruK are both enhanced.

The "sucrose non-PTS gene group" in the invention refers to a gene group involved in the non-PTS system from among sucrose assimilation pathways of a microorganism. Specifically, it is a gene group consisting of a repressor protein (cscR), a sucrose hydrolase (cscA), a fructokinase (cscK), and a sucrose permease (cscB). When a gene of the sucrose non-PTS gene group is selected in the invention, one gene of, or two or more genes of, the sucrose non-PTS gene group may be selected, and examples thereof include cscA alone, a combination of cscA and cscK, a combination of cscA and cscB, a combination of cscA and cscR, a combination of cscA, cscB, and cscR, and a combination of cscA, cscK, and cscR. Among them, it is preferable to select cscA alone from the viewpoint of more efficiently producing lactic acid. In a specific embodiment of the invention, it is preferable to select "one gene of, or two or more genes of, the sucrose non-PTS gene group" other than a combination of repressor protein (cscR), sucrose hydrolase (cscA), fructokinase (cscK) and sucrose permease (cscB) and a combination of sucrose hydrolase (cscA), fructokinase (cscK) and sucrose permease (cscB)

The sucrose hydrolase (invertase, CscA) in the invention is a generic term for enzymes that are classified to enzyme number 3.2.1.26 according to the enzyme committee report of the International Union of Biochemistry (I.U.B.), and that catalyze a reaction of generating D-glucose and D-fructose from sucrose.

This enzyme is an enzyme that an *Escherichia coli* such as K12 strain does not naturally possess, and this enzyme is one of the enzymes of the non-PTS metabolism pathway including a proton co-transporter, an invertase, a fructokinase, and a sucrose-specific repressor (see Canadian Journal of Microbiology, (1991) vol. 45, pp 418-422). In the invention, as a result of the impartment of cscA alone, sucrose outside the bacterial cell is decomposed into glucose and fructose at the periplasm and released to outside the cell, and they are phosphorylated and incorporated into the cytoplasm via a glucose PTS and a fructose PTS. As a result, fructose can be supplied to a fructose metabolism system of the bacterium, and can be assimilated using a glycolytic system.

As the gene of the sucrose hydrolase (invertase, CscA) to be introduced into the host bacterium according to the invention, a DNA having the base sequence of a gene that encodes a sucrose hydrolase (invertase, CscA) and that is obtained from an organism having the enzyme, or a synthetic DNA sequence synthesized based on a known base sequence of the gene, may be used. Preferable examples thereof include those derived from bacteria belonging to the genus *Erwinia*, bacteria belonging to the genus *Proteus*, bacteria belonging to the genus *Vibrio*, bacteria belonging to the genus *Agrobacterium*, bacteria belonging to the genus *Rhizobium*, bacteria belonging to the genus Staphylococcus, bacteria belonging to the genus *Bifidobacterium*, and bacteria belonging to the genus *Escherichia*. Examples thereof include a DNA having the base sequence of a gene derived from an *Escherichia coli* O157 strain. A DNA having the base sequence of a gene derived from an *Escherichia coli* O157 strain is particularly preferable. Further, it is preferable that a signal sequence for transferring the CscA to the periplasm of the bacterial cell is added to the CscA.

As the gene of the repressor protein (CscR) to be introduced into the host bacterium according to the invention, a DNA having the base sequence of a gene that encodes a repressor protein (CscR) and that is obtained from an organism having the enzyme, or a synthetic DNA sequence synthesized based on a known base sequence of the gene, may be used. Preferable examples thereof include those derived from bacteria belonging to the genus *Erwinia*, bacteria belonging to the genus *Proteus*, bacteria belonging to the genus *Vibrio*, bacteria belonging to the genus *Agrobacterium*, bacteria belonging to the genus *Rhizobium*, bacteria belonging to the genus Staphylococcus, bacteria belonging to the genus *Bifi-*

*dobacterium*, and bacteria belonging to the genus *Escherichia*. Examples thereof include a DNA having the base sequence of a gene derived from an *Escherichia coli* O157 strain. A DNA having the base sequence of a gene derived from an *Escherichia coli* O157 strain is particularly preferable.

As the gene of the fructokinase (CscK) to be introduced into the host bacterium according to the invention, a DNA having the base sequence of a gene that encodes a fructokinase (CscK) and that is obtained from an organism having the enzyme, or a synthetic DNA sequence synthesized based on a known base sequence of the gene, may be used. Preferable examples thereof include those derived from bacteria belonging to the genus *Erwinia*, bacteria belonging to the genus *Proteus*, bacteria belonging to the genus *Vibrio*, bacteria belonging to the genus *Agrobacterium*, bacteria belonging to the genus *Rhizobium*, bacteria belonging to the genus *Staphylococcus*, bacteria belonging to the genus *Bifidobacterium*, and bacteria belonging to the genus *Escherichia*. Examples thereof include a DNA having the base sequence of a gene derived from an *Escherichia coli* O157 strain. A DNA having the base sequence of a gene derived from an *Escherichia coli* O157 strain is particularly preferable.

As the gene of the sucrose permease (CscB) to be introduced into the host bacterium according to the invention, a DNA having the base sequence of a gene that encodes a sucrose permease (CscB) and that is obtained from an organism having the enzyme, or a synthetic DNA sequence synthesized based on a known base sequence of the gene, may be used. Preferable examples thereof include those derived from bacteria belonging to the genus *Erwinia*, bacteria belonging to the genus Proteus, bacteria belonging to the genus *Vibrio*, bacteria belonging to the genus *Agrobacterium*, bacteria belonging to the genus *Rhizobium*, bacteria belonging to the genus *Staphylococcus*, bacteria belonging to the genus *Bifidobacterium*, and bacteria belonging to the genus *Escherichia*. Examples thereof include a DNA having the base sequence of a gene derived from an *Escherichia coli* O157 strain. A DNA having the base sequence of a gene derived from an *Escherichia coli* O157 strain is particularly preferable.

The fructose-1-phosphate kinase (FruK) in the invention is an enzyme classified to enzyme number 2.7.1.56 according to the enzyme committee report of the International Union of Biochemistry (I.U.B.), and is also referred to as "phosphofructokinase 1". Uptake of fructose by bacteria, such as *Escherichia coli*, is generally suppressed in the presence of glucose. Heretofore, there has been no finding that enhanced expression of FruK promotes uptake of fructose even in the presence of glucose, and contributes to improvement in efficiency of production of D-lactic acid in a D-lactic acid-producing bacterium. Further, it is unexpected that the efficiency of production of lactic acid is improved by enhancement of expression of fruK alone in a series of fructose metabolism systems, subsequent to uptake of fructose generated from sucrose by the CscA into the cell and metabolism thereof into fructose-1-phosphate.

As the gene of the fructose-1-phosphate kinase (FruK) to be introduced into a host *Escherichia coli* according to the invention, a DNA having the base sequence of a gene that encodes fructose-1-phosphate kinase (FruK) and that is obtained from an organism possessing this enzyme, or a synthetic DNA sequence synthesized based on a known base sequence of the gene, may be used. Preferable examples thereof include those derived from bacteria belonging to the genus *Escherichia*, bacteria belonging to the genus *Pseudomonas*, bacteria belonging to the genus *Aerobacter*, and bacteria belonging to the genus *Clostridium*, particularly bacteria belonging to the genus *Escherichia*. Examples thereof include a DNA having the base sequence of a gene derived from an *Escherichia coli* MG1655 strain. A DNA having the base sequence of a gene derived from an *Escherichia coli* MG1655 strain is particularly preferable.

In the invention, it is more preferable that each of sucrose hydrolase (CscA) and fructose phosphate kinase is obtained by introduction of a gene encoding the corresponding protein derived from *Escherichia coli* O157 or *Escherichia coli* MG1655. Use of genes derived from such bacteria ensures expression of functions.

In the D-lactic acid-producing bacterium according to the invention, FruR activity is preferably inactivated or attenuated from the viewpoint of the capability of promoting uptake of fructose.

The gene of FruR of which the activity is to be attenuated in the invention is not limited as long as the gene is an innate gene of the host bacterium, and may be a DNA having the base sequence of the innate gene of the host bacterium that encodes FruR, or a synthetic DNA sequence introduced based on a known base sequence of the gene.

D-lactic acid can be rapidly produced with high optical purity by using the D-lactic acid-producing bacterium in the production method described below.

<L-Lactic Acid-Producing Bacterium>

In the L-lactic acid-producing bacterium according to the invention, NAD-dependent L-lactate dehydrogenase activity is preferably enhanced as the enhancement of an NAD-dependent lactate dehydrogenase activity.

The L-lactate dehydrogenase which is used as the NAD-dependent lactate dehydrogenase in the invention and of which the activity is to be enhanced refers to an enzyme that produces L-lactic acid and NAD from pyruvic acid and NADH. The gene of the NAD-dependent L-lactate dehydrogenase may be a DNA having the base sequence of a gene that is obtained from an organism having the activity of this enzyme, or a synthetic DNA sequence synthesized based on a known base sequence of the gene.

A preferable NAD-dependent L-lactate dehydrogenase gene is not particularly limited as long as the gene is capable of expressing in *Escherichia coli* and encodes a NAD-dependent L-lactate dehydrogenase capable of producing L-lactic acid. Preferable examples thereof include NAD-dependent L-lactate dehydrogenases derived from the genus *Bifidobacterium*, the genus *Enterobacter*, the genus *Lactococcus*, and the genus *Lactobacillus*. The NAD-dependent L-lactate dehydrogenase gene is preferably NAD-dependent L-lactate dehydrogenase (Ldh2) derived from *Bifidobacterium longum*, particularly from the viewpoint of the efficiency of production of lactic acid.

One example of the measure to enhance NAD-dependent L-lactate dehydrogenase activity is use of the promoter described in connection with ldhA in the D-lactic acid-producing *Escherichia coli*, to which the above explanation is directly applicable. When the bacterium with enhanced L-lactate dehydrogenase activity is used in the production of L-lactic acid under aerobic conditions, the accumulation amount of L-lactic acid is increased, and the optical purity of L-lactic acid can be improved, compared to a case in which the expression of L-lactate dehydrogenase is not enhanced.

It is preferable that the activity of Dld as the NAD-independent lactate oxidoreductase in the L-lactic acid-producing bacterium according to the invention is enhanced, from the viewpoint of improving the optical purity.

The FAD-dependent D-lactate dehydrogenase (Dld) in the invention is classified to enzyme number 1.1.2.4 according to the enzyme committee report of the International Union of Biochemistry (I.U.B.), and is a generic name for enzymes that catalyze a reaction of generating pyruvic acid from D-lactic acid in the presence of oxidized flavin adenine dinucleotide serving as a coenzyme.

The dld gene that can be introduced into a host bacterium in order to enhance the activity of Dld may be derived from any microorganism, and examples thereof include those derived from bacteria belonging to the genus *Escherichia*, bacteria belonging to the genus *Corynebacterium*, and bacteria belonging to the genus *Zymomonas*.

In particular, from the viewpoint of improving the optical purity, the dld gene is more preferably at least one dld gene selected from the group consisting of *Escherichia coli*, *Zymomonas*, and *Corynebacterium* dld genes, which have a Lact deh memb domain in common, and each of which is particularly preferably derived from *Escherichia coli*, *Corynebacterium glutamicum*, or *Zymomonas mobilis*. The dld genes of the genus *Zymomonas* and the genus *Corynebacterium* further have a FAD oxidase domain in common. The Lact deh memb domain is an amino acid sequence that lactate dehydrogenases located at the cell membrane possess in common with high similarity.

The information about the presence or absence of the sequence of the Lact deh memb domain or the FAD oxidase domain is obtained by inputting and searching the amino acid sequence of an enzyme using Pfam database (Nucleic Acids Research (2008) Database Issue 36:D281-D288) or the like. For example, the presence or absence of the sequence of the Lact deh memb domain or the FAD oxidase domain in a desired amino acid sequence can be confirmed by inputting the amino acid sequence to http://pfam.sanger.ac.uk/search, followed by searching with initial setting.

In a case in which there is a control factor that inhibits the transcription of the gene of NAD-independent lactate dehydrogenase activity, the enhancement of the NAD-independent lactate dehydrogenase activity may be attenuation or inactivation of the factor.

One example of the measure to enhance Dld activity is use of the promoter described in connection with ldhA in the D-lactic acid-producing *Escherichia coli*, to which the above explanation is directly applicable.

Further, it is preferable that at least one selected from the group consisting of LdhA activity, LldD activity, and Pfl activity in the L-lactic acid-producing bacterium according to the invention is inactivated or attenuated.

With regard to details about LdhA, LldD, and Pfl of which the activity is to be inactivated or attenuated, the details thereof described above are directly applicable.

Decomposition of pyruvic acid, which is a raw material for the production of L-lactic acid, can be inhibited by inactivating or attenuating LdhA activity.

Consumption of L-lactic acid, which is a product, can be inhibited by inactivating or attenuating LldD activity.

In addition to the above, it is preferable that at least one selected from the group consisting of Mdh activity and AspA activity in the L-lactic acid-producing bacterium according to the invention is inactivated or attenuated, from the viewpoint of suppressing the amount of by-products produced, similarly to the case of the D-lactic acid-producing bacterium described above.

Further, in order to enable the production of L-lactic acid using another sugar as a raw material, at least one selected from the group consisting of CscA and FruK in the L-lactic acid-producing bacterium according to the invention may be enhanced, similarly to the case of the D-lactic acid-producing bacterium described above; it is more preferable that both CscA and FruK are enhanced. Further, in the L-lactic acid-producing bacterium according to the invention, the activity of FruR is preferably inactivated or attenuated from the viewpoint of providing capability of promoting uptake of fructose.

With regard to details about Mdh and AspA, sucrose non-PTS gene group, FruK, and FruR that are to be inactivated or attenuated or enhanced, the details thereof described above are directly applicable.

<Method of Producing Lactic Acid>

Next, the method of producing lactic acid according to the invention is described below.

The method of producing lactic acid according to the invention is a method of producing lactic acid using the lactic acid-producing bacterium described above.

In particular, D-lactic acid can be produced with high optical purity and high efficiency by culture using the D-lactic acid-producing bacterium described above. Similarly, L-lactic acid can be produced with high optical purity and high efficiency by culture using the L-lactic acid-producing bacterium described above.

The method of producing lactic acid according to the invention includes, specifically: culturing the lactic acid-producing bacterium in a culture liquid; and collecting a specific lactic acid produced by the lactic acid-producing bacterium, from the culture obtained by the cultivation.

In the method of producing lactic acid according to the invention, a plant-derived raw material that is commonly used as a raw material for lactic acid production may be used. The plant-derived raw material may be any carbon source obtained from a plant. Specifically, the scope of the plant-derived raw material encompasses organs such as roots, stems, trunks, branchs, leafs, flowers, or seeds, plant bodies including the organs, and decomposition products of the plant organ. Further, carbon sources that are obtained from plant bodies, plant organs, or decomposition products thereof, and that can be used by microorganisms as carbon sources during cultivation are also included in the scope of the plant-derived raw material.

General examples of the carbon source included in the plant-derived raw material include: saccharides such as starch, glucose, fructose, xylose, and arabinose; wood and herbaceous decomposition products containing these saccharide components at high contents; cellulose hydlysates containing these saccharide components at high contents; and combinations thereof. Further, vegetable oil-derived glycerin or fatty acids may also be included in the scope of the carbon source according to the invention.

In particular, when the lactic acid-producing *Escherichia coli* according to the invention has CscA activity, the lactic acid-producing *Escherichia coli* has a sucrose assimilation ability; therefore, the lactic acid-producing *Escherichia coli* conducts successful assimilattion to produce lactic acid even when a sucrose-containing plant raw material is used.

Preferable examples of the plant-derived raw material in the invention include agricultural crops such as cereal, corn, rice, wheat, soybean, sugarcane, beet, cotton, and combinations thereof. The form thereof when used as a raw material is not particularly limited, and may be an unprocessed material, a juice, a crushed material, or the like. Further, the plant-derived raw material may take a form consisting of the carbon source(s) only.

The blending of the plant-derived raw material and the lactic acid-producing bacterium may vary depending on the activity of the lactic acid-producing bacterium. In general, the initial sugar concentration (in terms of glucose-equivalent concentration) as the concentration of the plant-derived raw material in the medium may be 20% by mass or lower relative to the total mass of the mixture, and the initial sugar concentration is preferably 15% by mass or lower from the viewpoint of the sugar tolerance of bacterium. Other components may be added in usual amounts for addition to a microbial medium, and the amounts thereof are not particularly limited.

The content of the lactic acid-producing bacterium in the medium may vary depending on the kind and activity of bacterium. In general, the initial bacterial concentration may be from 0.1% by mass to 30% by mass, and preferably from 1% by mass to 10% by mass, relative to the culture liquid, from the viewpoint of controlling culture conditions.

The cultivation in the invention refers to culturing the microorganism according to the invention using a medium. The medium to be used is not particularly limited if the medium contains a carbon source, a nitrogen source, an inorganic ion, and organic trace elements, nucleic acids, vitamins, and the like, which are required by the microorganism in order to produce lactic acid.

In particular, it is preferable to conduct cultivation using a medium added with two or more amino acids, from the viewpoint of production rate. The medium added with two or more amino acids in the invention means a medium that includes at least two amino acids from among various naturally-occurring amino acids, and the scope thereof encompasses a medium that includes a hydrolysate of a natural product or natural product extract, such as yeast extract, casamino acid, peptone, whey, blackstrap molasses, and corn steep liquor. In order to obtain more favorable results, a medium that includes at least one selected from yeast extract, peptone, whey, blackstrap molasses, or corn steep liquor, or a mixture of, at a content of from 0.5% by mass to 20% by mass is preferable, and the content is more preferably from 2% by mass to 15% by mass. Especially, the addition of corn steep liquor produces a large effect, in which case non-addition of salts such as ammonium sulfate sometime produces better results. The medium is usually a liquid medium.

The culture conditions vary depending on the bacteria prepared and the culture apparatus. For example, the cultivation temperature during cultivation is preferably from 20° C. to 40° C., and more preferably from 25° C. to 35° C. The pH during cultivation is preferably from 6.0 to 8.0, and more preferably 7.0 to 7.6, by adjustment with NaOH, $NH_3$, or the like. The cultivation time is not particularly limited, and is a period of time necessary for the bacteria to grow sufficiently and produce lactic acid.

The cultivation is generally carried out using a culture vessel capable of controlling the temperature, pH, aerobic conditions, and stirring speed. However, the use of a culture vessel is not essential in the cultivation according to the invention. In a case in which cultivation is conducted using a culture vessel, if necessary, seed cultivation may be carried out in advance as a preculture, and a required amount of the resultant culture may be inoculated into a medium in a culture vessel that has been prepared in advance.

The culture product in the invention refers to bacterial cells and a culture liquid that are produced by the method described above, and processed products thereof.

In a case in which lactic acid is to be collected from the culture liquid, the method of collecting lactic acid from the culture product thus obtained, such as the culture liquid, may be a commonly known method, and examples thereof include: a method of directly distilling after acidification; a method of allowing lactide to form and distilling; a method of adding an alcohol and a catalyst so as to cause esterification, and then distilling the resultant; a method of extracting in an organic solvent; a method of separating using an ion exchange column; a method of concentrating and separating by electrodialysis; and combinations thereof. Further, since the bacterial cell produced by the method according to the invention produces a group of enzymes suitable for production of lactic acid, production of lactic acid using the bacterial cell and collection of lactic acid produced is also regarded as an embodiment of the method of collecting lactic acid from the culture product.

With the method of producing lactic acid according to the invention, lactic acid with high optical purity can be produced. Therefore, D-lactic acid or L-lactic acid can be obtained with high purity by collecting lactic acid contained in the culture product.

Production of lactic acid by culturing the microorganism obtained in the invention may be carried out without conducting aeration at all; however, aeration is preferably conducted in order to obtain more favorable results. Here, "under aeration conditions" does not necessarily require passage of the air through the culture liquid, and the scope thereof encompasses, depending on the shape of the culture vessel, surface aeration in which an air layer above the culture liquid is substituted while the culture liquid is stirred moderately; "under aeration conditions" refers to allowing an oxygen-containing gas to flow into the culture vessel. In the case of aeration into the liquid, the dissolved oxygen concentration varies with the combination of internal pressure, stirring blade position, stirring blade shape, and stirring speed. Therefore, the optimal conditions can be determined as follows using lactic acid production efficiency, the amount of organic acids other than lactic acid, or the like as indicators.

For example, in a case in which 500 g culture liquid is used for cultivation in a relatively small culture vessel such as a culture apparatus BMJ-01 manufactured by ABLE Corporation, favorable results can be obtained under aeration conditions that can be achieved with an aeration rate of from 0.01 vvm to 1 vvm and a stirring speed of from 50 rpm to 500 rpm at normal pressure, more preferably at an aeration rate of from 0.1 vvm to 0.5 vvm and a stirring speed of from 100 rpm to 400 rpm at normal pressure. These aeration/stirring conditions enable oxygen supply of an oxygen-transfer coefficient kLa of from 1/h to 400/h with respect to water at a temperature of 30° C. at normal pressure.

Further, another indicator of the optimal aeration condition is an aeration condition achieved with an aeration rate and a stirring speed at which the total amount of formic acid, acetic acid, succinic acid, ethanol, or a combination thereof that are produced by the pGAP-cscA-lox-lldD/ MG1655ΔpflΔdldΔmdhΔaspΔfruR/GAPldhA genome-inserted variant in anaerobic culture is 5.0 g/L or less, and more preferably 1.0 g/L or less, and at which lactic acid is produced.

Further, another indicator of the optimal aeration condition is a condition achieved by an aeration rate and a stirring speed at which the pGAP-cscA-lox-lldD/ MG1655ΔpflΔdldΔbmdhΔaspΔfruR/GAPldhA genome-inserted variant cultured in a medium containing 0.3% L-lactic acid, which is an optical isomer, decreases the concentration of L-lactic acid in the medium to 0.02% by mass or less within from 10 hours to 100 hours.

The aeration conditions described above do not need to be implemented all the time from the start to the end of the cultivation, and favorable results can also be obtained by implementing the aeration conditions for a part of the duration of the cultivation process. The efficiency of the production of lactic acid can be improved and an optical isomer can be reduced, by conducting the aeration in the above-described manner, According to the method of producing lactic acid according to the invention, L-lactic acid or D-lactic acid can be obtained with high optical purity. Further, even when the other optical isomer, which deteriorates the optical purity, is included in the raw material, the desired optical isomer can be produced by decomposing the undesired optical isomer.

In the method of producing lactic acid according to the invention, optical purity can be determined by using a common HPLC or a F-Kit D-/L-lactic acid (Product code 1112821, J.K. International Inc.). Desired L- or D-lactic acid with optical purity of 98% e.e. or higher can be obtained, and, preferably, a desired L- or D-lactic acid with optical purity of 99.5% e.e. or higher can be obtained, wherein the optical purity is calculated according to the following equation from the amount of L-lactic acid and amount of D-lactic acid in the resultant supernatant as measured using the F-Kit.

Optical purity (% e.e.)=100×(D-lactic acid concentration−L-lactic acid concentration)/(D-lactic acid concentration+L-lactic acid concentration)

In the equation, lactic acid concentrations are based on mass. According to the method of producing lactic acid according to the invention, an optical isomer with such a high optical purity as described above can be rapidly produced, as compared to a case in which D-lactic acid or L-lactic acid is produced using an *Escherichia coli* in which NAD-dependent lactate dehydrogenase and NAD-independent lactate oxidoreductase are not both enhanced.

EXAMPLES

Hereinafter, the invention is described in detail with reference to the following examples. However, the invention is not limited thereto. Unless otherwise specified, "%" and "part(s)" refer to "% by mass" and "part(s) by mass", respectively.

—D-Lactic Acid-Producing Bacterium—

Example 1

<Preparation of Dld Gene-deleted *Escherichia coli* MG1655 Variant

The entire base sequence of the genomic DNA of *Escherichia coli* is known (GenBank accession number: U00096), and the base sequence of a gene encoding FAD-dependent D-lactate dehydrogenase of *Escherichia coli* (hereinafter, referred to simply as "Dld") has also been reported (GenBank accession number: M10038).

Based on the gene information of regions of *Escherichia coli* MG1655 strain genomic DNA adjacent to the did gene, four kinds of oligonucleotide primer, CAACACCAAGCTTTCGCG (SEQ ID NO: 1), TTCCACTCCTTGTGGTGGC (SEQ ID NO: 2), AACTGCAGAAATTACGGATGGCAGAG (SEQ ID NO: 3), and TGTTCTAGAAAGTTCTTTGAC (SEQ ID NO: 4), were synthesized.

A genomic DNA of *Escherichia coli* MG1655 strain was prepared according to the method described in Current Protocols in Molecular Biology (John Wiley & Sons). PCR was conducted under usual conditions using the resultant genomic DNA as a template and using the primers of SEQ ID NO: 1 and SEQ ID NO: 2, as a result of which a DNA fragment of about 1.4 kbp (hereinafter sometimes referred to as "dld-L fragment") was amplified. PCR was conducted under usual conditions using the genomic DNA as a template and using the primers of SEQ ID NO: 3 and SEQ ID NO: 4, as a result of which a DNA fragment of about 1.2 kbp (hereinafter sometimes referred to as "dld-R fragment") was amplified. The resultant dld-L fragment was digested with restriction enzymes HindIII and PstI, and the resultant did-R fragment was digested with restriction enzymes PstI and XbaI. These digested fragments were mixed with a fragment that had been obtained by digesting a temperature-sensitive plasmid pTH18cs1 (Hashimoto-Gotoh, T., et al., Gene, Vol. 241(1), pp 185-191 (2000)) with HindIII and XbaI, and the fragments were ligated using a ligase. Thereafter, DH5α competent cell (DNA-903, Toyobo Co., Ltd.) was transformed with the ligation product, and a transformant that grew on an LB agar plate containing 10 μg/mL chloramphenicol at 30° C. was obtained. The resultant colony was cultured overnight at 30° C. in an LB liquid medium containing 10 μg/mL chloramphenicol. Then, a plasmid was recovered from the resultant bacterial cells. The plasmid obtained was named "pTHΔdld".

Further, the *Escherichia coli* MG1655 strain is available from American Type Culture Collection (ATCC), which is a bank for cells, microorganisms, and genes.

Example 2

A MG1655 strain was transformed with the plasmid pTH-Δdld obtained in Example 1 at 30° C., and a transformant that grew on an LB agar plate containing 10 μg/mL chloramphenicol was obtained. The resultant transformant was applied onto an agar plate, and cultured overnight at 30° C. Next, in order to obtain cultured bacterial cells thereof, the cultured transformant was applied onto an LB agar plate containing 10 μg/mL chloramphenicol, as a result of which a colony that grew at 42° C. was obtained.

Further, the operation of obtaining single colonies that grew at 42° C. was repeated again, thereby selecting a clone in which the entire plasmid was integrated into the chromosome by homologous recombination. It was confirmed that the clone did not have the plasmid in the cytoplasm.

Next, the above-mentioned clone was applied onto an LB agar plate, cultured overnight at 30° C., inoculated into an LB liquid medium (3 mL/test tube), and then cultured with shaking at 42° C. for from 3 hours to 4 hours. This was appropriately diluted (about $10^{-2}$-fold to $10^{-6}$-fold) in order to obtain single colonies, and the diluted liquid was applied onto an LB agar plate, and cultured overnight at 42° C., as a result of which colonies were obtained. From the colonies that appeared, 100 colonies were randomly picked up, and were each allowed to grow on an LB agar plate, and on an LB agar plate containing 10 μg/mL chloramphenicol. Chloramphenicol-sensitive clones that grew only on the LB agar plate were selected. Further, a fragment of about 2.0 kb containing dld was amplified by PCR using the chromosomal DNA of each of these target clones, and a variant in which a dld gene region was deleted was selected. The clone that passed the above selections was considered as a dld-deleted variant, and the resultant variant was named "MG1655Δdld variant".

Example 3

<Preparation of Pfl and Dld Genes-deleted Variant of *Escherichia coli* MG1655>

The entire base sequence of the genomic DNA of *Escherichia coli* is known (GenBank accession number: U00096), and the base sequence of a gene encoding pyruvate-formate lyase of *Escherichia coli* (hereinafter sometimes referred to as "Pfl") has also been reported (GenBank accession number: AE000192). In order to clone regions adjacent to the base sequence of the gene encoding Pfl, four kinds of oligonucleotide primer, GCACGAAAGCTTTGATTACG (SEQ ID NO: 5), TTATTGCATGCTTAGATTTGACTGAAATCG (SEQ ID NO: 6), TTATTGCATGCTTATTTACTGCGTACTTCG (SEQ ID NO: 7), and AAGGCCTACGAAAAGCTGCAG (SEQ ID NO: 8), were synthesized.

PCR was conducted under usual conditions using the genomic DNA of *Escherichia coli* MG1655 strain as a template and using the primers of SEQ ID NO: 5 and SEQ ID NO: 6, as a result of which a DNA fragment of about 1.8 kbp (hereinafter sometimes referred to as "pflB-L fragment") was amplified. PCR was conducted under usual conditions using the genomic DNA of *Escherichia coli* MG1655 strain as a template and using the primers of SEQ ID NO: 7 and SEQ ID NO: 8, as a result of which a DNA fragment of about 1.3 kbp (hereinafter sometimes referred to as "pflB-R fragment") was amplified. These DNA fragments were separated by agarose electrophoresis and recovered, and the pflB-L fragment was digested with HindIII and SphI and the pflB-R fragment was digested with SphI and PstI, respectively. These two kinds of digested fragments and a product obtained by digesting a temperature-sensitive plasmid pTH18cs1 (GenBank accession number: AB019610) with HindIII and PstI were allowed to react in the presence of T4 DNA ligase. Thereafter, an *Escherichia coli* DH5α competent cell (DNA-903, Toyobo Co., Ltd.) was transformed with the ligation product, as a result of which a plasmid containing two fragments—the 5'-upstream adjacent fragment and the 3'-downstream adjacent fragment—of the pflB gene was obtained and named "pTHΔpfl".

The MG1655Δdld variant obtained in Example 2 was transformed with the obtained plasmid pTHΔpfl, and a transformant that grew at 30° C. on an LB agar plate containing 10 μg/mL chloramphenicol was obtained. The resultant transformant was applied onto an agar plate, and cultured overnight at 30° C. Next, in order to obtain cultured bacterial cells thereof, the cultured transformant was applied onto an LB agar plate containing 10 μg/mL chloramphenicol, as a result of which colonies that grew at 42° C. were obtained.

The pfl gene-disrupted MG1655Δdld variant was obtained from the resultant clone according to a method similar to that employed in Example 2, and was named "MG1655ΔpflΔdld variant".

Example 4

<Preparation of *Escherichia coli* MG1655ΔpflΔdldΔmdh Variant>

The entire base sequence of the genomic DNA of *Escherichia coli* is known (GenBank accession number: U00096), and the base sequence of an mdh gene of *Escherichia coli* has also been reported (Genbank accession number AE000403). In order to clone regions adjacent to the base sequence of the gene (939 bp) encoding Mdh, four kinds of oligonucleotide primer, AAAGGTACCAGAATACCTTCTGCTTTGCCC (SEQ ID NO: 9), AAAGGATCCCCTAAACTCCTTATTATATTG (SEQ ID NO: 10), AAAGGATCCAAACCGGAGCACAGACTCCGG (SEQ ID NO: 11), and AAATCTAGAATCAGATCATCGTCGCCTTAC (SEQ ID NO: 12), were synthesized.

PCR was conducted under usual conditions using the genomic DNA of *Escherichia coli* MG1655 strain as a template and using a primer combination of SEQ ID NO: 9 and SEQ ID NO: 10, as a result of which a DNA fragment of about 800 by (hereinafter sometimes referred to as "mdh-L fragment") was amplified. PCR was conducted under usual conditions using the genomic DNA of *Escherichia coli* MG1655 strain as a template and using a primer combination of SEQ ID NO: 11 and SEQ ID NO: 12, as a result of which a DNA fragment of about 1000 by (hereinafter sometimes referred to as "mdh-R fragment") was amplified. These DNA fragments were separated by agarose electrophoresis and recovered. The mdh-L fragment was digested with KpnI and BamHI, and the mdh-R fragment was digested with BamHI and XbaI. These two kinds of digested fragment, and a product obtained by digesting a temperature-sensitive plasmid pTH18cs1 (GenBank accession number: AB019610) with KpnI and XbaI, were allowed to react in the presence of T4 DNA ligase. Thereafter, an *Escherichia coli* DH5α competent cell (DNA-903, Toyobo Co., Ltd.) was transformed with the ligation product, as a result of which a plasmid containing two fragments—the 5'-upstream adjacent fragment and the 3'-downstream adjacent fragment—of the gene encoding mdh was obtained, and the obtained plasmid was named "pTHΔmdh".

The *Escherichia coli* MG1655ΔpflΔdld variant obtained in Example 3 was transformed with the plasmid pTHΔmdh, and an mdh gene-disrupted MG1655ΔpflΔdld variant was prepared according to a method similar to that employed in Example 2. This variant was named "MG1655ΔpflΔdldΔmdh variant".

Example 5

<Preparation of *Escherichia coli* MG1655ΔpflΔdldΔmdhΔasp Variant>

The entire base sequence of the genomic DNA of *Escherichia coli* is known (GenBank accession number: U00096), and the base sequence of an *Escherichia coli* aspA gene has also been reported (GenBank accession number: AE000486). In order to clone regions adjacent to the base sequence of a gene (1,482 bp) encoding AspA, four kinds of oligonucleotide primer, TTTTGAGCTCGATCAGGATTGCGTTGGTGG (SEQ ID NO: 13), CGAACAGTAATCGTACAGGG (SEQ ID NO: 14), TACGATTACTGTTCGGCATCGACCGAATACCCGAG (SEQ ID NO: 15), and TTTTTCTAGACCTGGCACGCCTCTCTTCTC (SEQ ID NO: 16), were synthesized.

PCR was conducted under usual conditions using the genomic DNA of *Escherichia coli* MG1655 strain as a template and using a primer combination of SEQ ID NO: 13 and SEQ ID NO: 14, as a result of which a DNA fragment of about 910 by (hereinafter sometimes referred to as "aspA-L fragment") was amplified. PCR was conducted under usual conditions using the genomic DNA of *Escherichia coli* MG1655 strain as a template and using a primer combination of SEQ ID NO: 15 and SEQ ID NO: 16, PCR, as a result of which a DNA fragment of about 1,100 by (hereinafter sometimes referred to as "aspA-R fragment") was amplified. These DNA fragments were separated by agarose electrophoresis and recovered. Both of the aspA-L fragment and the aspA-R fragment were terminally blunted with a DNA Blunting Kit (Takara Bio Inc.), and then the 5'-terminals thereof were phosphorylated using T4 polynucleotide kinase according to a common method. Separately, a temperature-sensitive plasmid pTH18cs1 was digested with SmaI, and then subjected to dephosphorylation treatment using an alkaline phosphatase. The two kinds of phosphorylated fragment and the dephosphorylated plasmid were allowed to react in the presence of T4 DNA ligase. Thereafter, an *Escherichia coli* DH5α competent cell (DNA-903, Toyobo Co., Ltd.) was transformed with the ligation product, as a result of which a plasmid containing two fragments—the 5'-upstream adjacent fragment and the 3'-downstream adjacent fragment—of the gene encoding AspA was obtained. This plasmid was named "pTHΔasp".

The *Escherichia coli* MG1655ΔpflΔdldΔmdh variant obtained in Example 4 was transformed with the plasmid pTHΔasp, and finally aspA gene-disrupted MG1655ΔpflΔdldΔmdh variant was obtained, which was named "MG1655ΔpflΔdldΔmdhΔasp variant". The specific method for obtaining this variant was similar to the method described in Example 2 according to the invention.

Example 6

<Substituting GAPDH Promoter for ldhA Promoter on Genome of *Escherichia coli* MG1655ΔpflΔdldΔmdhΔasp Variant>

The base sequence of an *Escherichia coli* ldhA gene has been already reported (GenBank accession number: U36928). In order to obtain the glyceraldehyde-3-phosphate dehydrogenase (GAPDH) promoter, amplification by a PCR method was carried out using the genomic DNA of *Escherichia coli* MG1655 strain as a template and using AACGAAT-TCTCGCAATGATTGACACGATTC (SEQ ID NO: 17) and ACAGAATTCGCTATTTGTTAGTGAATAAAAGG (SEQ ID NO: 18). The resultant DNA fragment was digested with a restriction enzyme EcoRI, thereby providing a fragment of about 100 by that encoded a GAPDH promoter. In order to obtain the gene of D-lactate dehydrogenase (ldhA), amplification by a PCR method was carried out using the genomic DNA of *Escherichia coli* MG1655 strain as a template and using GGAATTCCGGAGAAAGTCTTATGAAACT (SEQ ID NO: 19) and CCCAAGCTTTTAAACCAGTTCGT-TCGGGC (SEQ ID NO: 20). The resultant DNA fragment was digested with restriction enzymes EcoRI and HindIII, thereby providing a D-lactate dehydrogenase (ldhA) gene fragment of about 1.0 kbp. The above two DNA fragments were mixed with a fragment obtained by digesting a plasmid pUC18 with restriction enzymes EcoRI and HindIII, and the mixed fragments were ligated using a ligase. Thereafter, an *Escherichia coli* DH5α competent cell (DNA-903, Toyobo Co., Ltd.) was transformed with the ligation product, and a transformant that grew on an LB agar plate containing 50 μg/mL ampicillin was obtained. The resultant colony was cultured in an LB liquid medium containing 50 μg/mL ampicillin overnight at 30° C., and a plasmid pGAP-ldhA was recovered from the resultant bacterial cells.

PCR was carried out using the genomic DNA of *Escherichia coli* as a template and using AAGGTACCACCA-GAGCGTTCTCAAGC (SEQ ID NO: 21) and GCTCTA-GATTCTCCAGTGATGTTGAATCAC (SEQ ID NO: 22), which were prepared based on the gene information of the *Escherichia coli* MG1655 strain at a 5'-adjacent region of the ldhA gene, thereby amplifying a DNA fragment of about 1000 bp.

Further, PCR was carried out using the plasmid pGAPldhA prepared above as a template and using GGTCTAGAG-CAATGATTCACACGATTCG (SEQ ID NO: 23) prepared based on the sequence information of a glyceraldehyde-3-phosphate dehydrogenase (GAPDH) promoter of *Escherichia coli* MG1655 strain, and AACTGCAGGTTCGTTCT-CATACACGTCC (SEQ ID NO: 24) prepared based on the sequence information of the ldhA gene of *Escherichia coli* MG1655 strain, as a result of which a DNA fragment of about 850 by that contained a GAPDH promoter and a region of the ldhA gene at or around the initiation codon was obtained.

The fragments obtained above were digested with restriction enzymes KpnI and XbaI, and XbaI and PstI, respectively. The resultant fragments were mixed with a fragment obtained by digesting a temperature-sensitive plasmid pTH18cs1 with KpnI and PstI, and the mixed fragments were ligated using a ligase. Thereafter, a DH5α competent cell (DNA-903, Toyobo Co., Ltd.) was transformed with the ligation product at 30° C., and a transformant that grew on an LB agar plate containing 10 μg/mL chloramphenicol was obtained. The resultant colony was cultured in an LB liquid medium containing 10 μg/mL chloramphenicol overnight at 30° C. A plasmid was recovered from the resultant bacterial cells, and was named "pTH-GAPldhA".

The *Escherichia coli* MG1655ΔpflΔdldΔmdhΔasp variant obtained in Example 5 was transformed with the obtained plasmid pTH-GAPldhA, and cultured on an LB agar plate containing 10 μg/mL chloramphenicol overnight at 30° C., as a result of which a transformant was obtained. The resultant transformant was inoculated into an LB liquid medium containing 10 μg/mL chloramphenicol, and cultured overnight at 30° C. Next, in order to obtain cultured bacterial cells thereof, the cultured transformant was applied onto an LB agar plate containing 10 μg/mL chloramphenicol, as a result of which a colony that grew at 42° C. was obtained. The resultant colony was cultured in an LB liquid medium not containing chloramphenicol overnight at 30° C., and further applied onto an LB agar plate not containing chloramphenicol, as a result of which a colony that grew at 42° C. was obtained.

From the colonies that appeared, 100 colonies were randomly picked up, and were each grown on an LB agar plate not containing chloramphenicol and an LB agar plate containing 10 μg/mL chloramphenicol, and chloramphenicol-sensitive clones were selected. Further, a fragment of about 800 by containing the GAPDH promoter and the ldhA gene was amplified by PCR using the chromosomal DNA of each of these target clones, and a variant in which the ldhA promoter region was replaced with the GAPDH promoter was selected. The clone that passed the above selections was named "MG1655ΔpflΔdldΔmdhΔasp/GAPldhA genome-inserted variant".

<Preparation of lldR-disrupted Variant>

A plasmid in which an lldR gene is disrupted was constructed according to the following method.

The base sequence of an lldR gene of *Escherichia coli* has already been reported (GenBank accession number U00096 3777077 to 3777853).

In order to clone a region adjacent to the base sequence of the gene encoding lldR, PCR was conducted using the genomic DNA of *Escherichia coli* as a template and using GGGAATTCGACATCATTCGCTCGTCTAT-TCTTTCGATA (SEQ ID NO: 25) and GGGTACCTTAAG-GAATCATCCACGTTAAGACAT (SEQ ID NO: 26), thereby amplifying a DNA fragment upstream of lldR, and the amplified fragment was then cleaved with restriction enzymes EcoRI and KpnI. Then, PCR was conducted using the genomic DNA of *Escherichia coli* as a template and using ATGGTACCCGGAGAAAGTCTTATGAT-TATTTCCGCAGCCAGCGATTATCG (SEQ ID NO: 27) and GATGTCGACCTATGCCGCATTCCCTTTCGCCATG (SEQ ID NO: 28) as primers, thereby amplifying a DNA fragment downstream of lldR, and the amplified fragment was then cleaved with restriction enzymes KpnI and SalI. These two kinds of digested fragment and a product obtained by digesting a temperature-sensitive plasmid pTH18cs1 (GenBank accession number: AB019610) with EcoRI and SalI were allowed to react in the presence of T4 DNA ligase. Thereafter, an *Escherichia coli* DH5α competent cell (trade name: DNA-903, Toyobo Co., Ltd.) was transformed with the ligation product, thereby providing a plasmid containing two fragments the 5'-upstream adjacent fragment and the 3'-downstream adjacent fragment of the LldD-encoding gene. This plasmid was named "pTHΔlldR".

The MG1655ΔpflΔdldΔmdhΔasp/GAPldhA genome-inserted variant was transformed with the obtained plasmid, and cultured on an LB agar plate containing 10 μg/mL chloramphenicol overnight at 30° C., as a result of which a transformant was obtained. The obtained transformant was inoculated into an LB liquid medium containing 10 μg/mL chloramphenicol, and cultured overnight at 30° C. Next, in order to obtain a cultured bacterial cell, the cultured transformant was applied onto an LB agar plate containing 10 μg/mL chloramphenicol, as a result of which a colony that grew at 42° C. was obtained. The obtained colony was cultured in an LB liquid medium not containing chloramphenicol overnight at 30° C., and further applied onto an LB agar plate not containing chloramphenicol, as a result of which a colony that grew at 42° C. was obtained.

From the colonies that appeared, 100 colonies were selected randomly, and were each allowed to grow on an LB agar plate not containing chloramphenicol and an LB agar plate containing 10 μg/mL chloramphenicol, and chloramphenicol-sensitive clones were selected. Further, a region at or around lldR was amplified by PCR using the chromosomal DNA of each of these target clones, and a variant in which the lldR region was deleted was selected. The clone that passed the above selections was named "MG1655ΔpflΔdldΔmdhΔaspΔlldR/GAPldhA genome-inserted variant".

Example 7

<Preparation of Escherichia coli MG1655ΔpflΔdldΔmdhΔaspΔfruR/GAPldhA Genome-inserted Variant>

The entire base sequence of Escherichia coli genomic DNA is known (GenBank accession number: U00096), and the base sequence of a fruR gene of Escherichia coli MG1655 has also been reported. That is, the fruR gene is described at 88028 to 89032 of Escherichia coli MG1655 strain genome sequence described at GenBank accession number U00096.

In order to clone regions adjacent to the base sequence of the fruR gene (1005 bp), four kinds of oligonucleotide primer, TACTGCAGATCTCAATAACCGCTATCTGG (SEQ ID NO: 29), GCTCTAGATAGCCATTGTACTGGTATGG (SEQ ID NO: 30), TATCTAGATGCTCAGCCGTAGCTAAGC (SEQ ID NO: 31), and CGAATTCATCCATCTGACATTCGCTGG (SEQ ID NO: 32), were synthesized.

PCR was conducted under usual conditions using the genomic DNA of Escherichia coli MG1655 strain as a template and using a primer combination of SEQ ID NO: 29 and SEQ ID NO: 30, as a result of which a DNA fragment of about 950 by (hereinafter sometimes referred to as "fruR-L fragment") was amplified. PCR was conducted under usual conditions using the genomic DNA of Escherichia coli MG1655 strain as a template and using a primer combination of SEQ ID NO: 31 and SEQ ID NO: 32, as a result of which a DNA fragment of about 880 by (hereinafter sometimes referred to as "fruR-R fragment") was amplified. These DNA fragments were separated by agarose electrophoresis and recovered. The fruR-L fragment was digested with PstI and XbaI, and the fruR-R fragment was digested with XbaI and EcoRI. These two kinds of digested fragment and a product obtained by digesting a temperature-sensitive plasmid pTH18cs1 (GenBank accession number: AB019610) with PstI and EcoRI were allowed to react in the presence of T4 DNA ligase. Thereafter, an Escherichia coli DH5α competent cell (DNA-903, Toyobo Co., Ltd.) was transformed with the ligation product, as a result of which a plasmid containing two fragments—the 5'-upstream adjacent fragment and the 3'-downstream adjacent fragment of the fruR gene—was obtained. This plasmid was named "pTHΔfruR".

The Escherichia coli MG1655ΔpflΔdldΔmdhΔasp/GAPldhA genome-inserted variant obtained in Example 6 was transformed with the plasmid pTHΔfruR, and a fruR gene-disrupted MG1655ΔpflΔdldΔmdhΔasp/GAPldhA genome-inserted variant was prepared in a manner similar to Example 2. This variant was named "MG1655ΔpflΔdldΔmdhΔaspΔfruR/GAPldhA genome-inserted variant".

Example 8

<Construction of Expression Vector for Escherichia coli O157-derived Sucrose Hydrolase (Invertase) Gene and Transformant with the Expression Vector>

The amino acid sequence of invertase of Escherichia coli O157 and the base sequence of the gene thereof have already been reported. That is, the invertase-encoding gene (cscA) is described at 3274383 to 3275816 of the Escherichia coli O157 strain genome sequence described at GenBank accession number AE005174. The base sequence of a promoter necessary for expressing the gene may be the promoter sequence of an Escherichia coli-derived glyceraldehyde-3-phosphate dehydrogenase (hereinafter sometimes referred to as GAPDH) that is described at 397-440 in the base sequence information of GenBank accession number X02662.

In order to obtain the GAPDH promoter, amplification by a PCR method was carried out using the genomic DNA of Escherichia coli MG1655 strain as a template and using CGAGCTACATATGCAATGATTGACACGATTCCG (SEQ ID NO: 33) and TCTAGAGCTATTTGTTAGTGAATAAAAGG (SEQ ID NO: 34). The resultant DNA fragment was digested with a restriction enzyme NdeI, thereby providing a DNA fragment of about 110 by corresponding to the GAPDH promoter. The resultant DNA fragment was mixed with a fragment obtained by digesting a plasmid pBR322 (GenBank accession number J01749) with restriction enzymes NdeI and PvuII, and the mixed fragments were ligated using a ligase. Thereafter, a competent cell of Escherichia coli DH5α strain (DNA-903, Toyobo Co., Ltd.) was transformed with the ligation product, and a transformant that grew on an LB agar plate containing 50 μg/mL ampicillin was obtained. The resultant colony was cultured in an LB liquid medium containing 50 μg/mL ampicillin overnight at 37° C., and a plasmid pBRgapP was recovered from the resultant bacterial cells.

In order to obtain the invertase gene, amplification by a PCR method was carried out using the genomic DNA (SIGMA-ALDRICH: IRMM449) of Escherichia coli O157 as a template and using GATCTAGACGGAGAAAGTCTTATGACGCAATCTCGATTGCATG (SEQ ID NO: 35) and ATGGTACCTTAACCCAGTTGCCAGAGTGC (SEQ ID NO: 36). The resultant DNA fragment was digested with a restriction enzyme XbaI, thereby providing an invertase gene fragment of about 1.4 kbp. The resultant DNA fragment was mixed with a fragment obtained by digesting the plasmid pBRgapP prepared above with restriction enzymes XbaI and PshAI, and the mixed fragments were ligated using a ligase. Thereafter, a competent cell of Escherichia coli DH5α strain (DNA-903, Toyobo Co., Ltd.) was transformed with the ligation product, and a transformant that grew on an LB agar plate containing 50 μg/mL ampicillin was obtained. The resultant colony was cultured in an LB liquid medium containing 50 μg/mL ampicillin overnight at 37° C., and a plasmid pGAP-cscA was recovered from the resultant bacterial cells.

A competent cell of MG1655ΔpflΔdldΔmdhΔaspΔfruR/GAPldhA genome-inserted variant prepared in Example 7 was transformed with the plasmid pGAP-cscA, and the resultant transformant was cultured in an Miller's LB Broth agar plate containing 50 μg/mL ampicillin overnight at 37° C., as a result of which an MG1655ΔpflΔdldΔmdhΔaspΔfruR/GAPldhA genome-inserted variant/pGAP-cscA variant was obtained.

Further, a competent cell of MG1655ΔpflΔdldΔmdhΔasp/GAPldhA genome-inserted variant prepared in Example 6 was transformed with the plasmid pGAP-cscA, and the resultant transformant was cultured in an Miller's LB Broth agar plate containing 50 μg/mL ampicillin overnight at 37° C., as a result of which an MG1655ΔpflΔdldΔmdhΔasp/GAPldhA genome-inserted variant/pGAP-cscA variant was obtained.

Example 9

<Isolation of Lox Gene>

Based on the base sequence of L-lactate oxidase disclosed in JP-A No. 10-248574, two kinds of oligonucleotide primer, ATTCTAGACGGAGAAAGTCTTATG-GAAAAAACATATCAAGCAGGTACAAATG (SEQ ID NO: 37) and CAGGTACCTTAAATAAAACGATTCT-CACGCAATTTTA (SEQ ID NO: 38), were designed and synthesized. The primer of SEQ ID NO: 37 has an XbaI recognition site and an SD sequence of ldhA at its 5'-terminal side. The primer of SEQ ID NO: 38 has a KpnI recognition site at its 5'-terminal side. A chromosomal DNA was isolated from *Enterococcus* sp. ATCC9625 (which is described as *Lactococcus lactis* (subsp. *Cremoris* IFO3427) in JP-A No. 10-248574). PCR was carried out using the isolated chromosomal DNA as a template, and an amplified DNA fragment was isolated. The amplified DNA fragment was purified, and digested with XbaI. The digested fragment was mixed with a fragment obtained by digesting the pBRgapP obtained in Example 8 with restriction enzymes XbaI and PshAI, and the fragments were ligated using a ligase. Thereafter, a competent cell of *Escherichia coli* DH5α strain (trade name: DNA-903, Toyobo Co., Ltd.) was transformed with the ligation product, and a transformant that grew on an LB agar plate containing 50 μg/mL ampicillin was obtained. The obtained colony was cultured in an LB liquid medium containing 50 μg/mL ampicillin overnight at 37° C. A plasmid pGAP-lox was recovered from the resultant bacterial cells.

The base sequence of the isolated lox gene was determined using a DNA sequencer.

Example 10

<Isolation of lldD>

The entire base sequence of the genomic DNA of *Escherichia coli* is known, and the base sequence of a gene encoding FMN-dependent L-lactate dehydrogenase of *Escherichia coli* (lldD) has also been reported (Genbank accession number U00096, 3777850 to 3779040). In order to clone the lldD, two kinds of oligonucleotide primer, ATTCTAGACG-GAGAAAGTCTTATGATTATTTCCGCAGC-CAGCGATTATCG (SEQ ID NO: 39) and GATGGTAC-CCTATGCCGCATTCCCTTTCGCCATG (SEQ ID NO: 40), were designed and synthesized.

The genomic DNA of *Escherichia coli* K12 strain was isolated by a common method, and PCR was carried out using the resultant DNA as a template. The amplified DNA fragment was purified, and digested with XbaI. The digested fragment was mixed with a fragment obtained by digesting the pBRgapP obtained in Example 8 with restriction enzymes XbaI and PshAI, and the fragments were ligated using a ligase. Thereafter, a competent cell of *Escherichia coli* DH5α strain (trade name: DNA-903, Toyobo Co., Ltd.)) was transformed with the ligation product, and a transformant that grew on an LB agar plate containing 50 μg/mL ampicillin was obtained. The obtained colony was cultured in an LB liquid medium containing 50 μg/mL ampicillin overnight at 37° C. A plasmid pGAP-lldD was recovered from the resultant bacterial cells. The base sequence of the isolated lldD was determined using a DNA sequencer.

<Construction of Mutated lldD>

In order to construct mutated lldD, a variant gene of lldD was constructed by PCR according to the protocol of GeneMorph (registered trademark) II Random Mutagenesis Kit (Stratagene), using oligonucleotide primers of SEQ ID NO: 39 and SEQ ID NO: 40 used in the above, and using the pGAP-lldD as a template. The amplified DNA fragment was purified, and digested with XbaI. The digested fragment was mixed with a fragment obtained by digesting the pBRgapP obtained in Example 8 with restriction enzymes XbaI and PshAI, and the fragments were ligated using a ligase. Thereafter, a competent cell of *Escherichia coli* DH5α strain (trade name: DNA-903, Toyobo Co., Ltd.)) was transformed with the ligation product, and a transformant that grew on an LB agar plate containing 50 μg/mL ampicillin was obtained. The obtained colony was seeded into a 96-well deep well plate that had a volume of 2 mL/well and to which 300 μL of a medium (1% glucose, 1.2% peptone, 2% yeast extract, (pH7.5)) had been added, and followed by culturing under stirring at 33° C. for 24 hours. After the cultivation was completed, bacterial cells were collected, and the supernatant was removed. Thereafter, 200 μL of bacteriolytic enzyme liquid (0.285 mg/mL Lysozyme, 1.5 U/mL DNaseI, 2 mM $MgCl_2$) was added thereto, and mixing by pipetting for 35 times was conducted. After incubation at 35° C. for 15 minutes, pipetting for mixing was further conducted 35 times, and the lysis of bacterial cells was confirmed visually. Thereafter, 10 μL thereof was taken and added to 190 μL of a reaction liquid (20 mg/mL phenazine methosulfate, 3 mg/mL 3-[4,5-dimethylthiazol-2-yl]-2,5-diphenyltetrazolium bromide 0.5 MKPB (pH7.0)). Then, 40 μL of 100 mM sodium L-lactate (pH 7.0) was added, and an increase rate of absorbance at 570 nm was observed.

A plasmid was extracted from a colony that exhibited a 1.5-fold or higher increase rate as compared to control, and the base sequence of the isolated mutated lldD was determined by a DNA sequencer. The sequence is set forth as SEQ ID NO: 41. The plasmid obtained was named "pGAP-mutated lldD".

<Construction of Plasmid with Co-Enhancement of Lox and LldD>

PCR was carried out using the pGAP-mutated lldD as a template and using ATCGTCGACCGGAGAAAGTCTTAT-GATTATTTCCGCAGCCAGCGATTATCG (SEQ ID NO: 42) and GATGTCGACCTATGCCGCATTC-CCTTTCGCCATG (SEQ ID NO: 28) as primers, as a result of which an lldD fragment was obtained. The lldD fragment was cleaved with a restriction enzyme SalI, and purified. The purified fragment was mixed with a fragment obtained by cleaving the pGAP-lox with a restriction enzyme SalI, and the fragments were ligated using a ligase. Thereafter, a competent cell of *Escherichia coli* DH5α strain (trade name: DNA-903, Toyobo Co., Ltd.)) was transformed with the ligation product, and a transformant that grew on an LB agar plate containing 50 μg/mL ampicillin was obtained. A plasmid pGAP-lox-mutated lldD was obtained from the obtained transformant. The insertion direction of the mutated lldD was confirmed by sequencing.

Example 11

<Isolation of lctO>

The base sequence of a gene encoding L-lactate oxidase of *Lactococcus lactic* IL1403 has been disclosed (Genbank accession number AE006357, 4813 to 3662). Based on the base sequence information, two kinds of oligonucleotide primer, AATTCTAGACGGAGAAAGTCTTATG-CATCTATCATCTACAGATGTAAACTTTA (SEQ ID NO: 43) and ACAGGTACCTTAGTCAATCAATGAGG-TATGTTTGATTT (SEQ ID NO: 44), were designed and synthesized, in order to isolate the L-lactate oxidase gene from *L. lactis* subsp. *lactis* ATCC 19435. The primer of SEQ ID NO: 43 has an XbaI recognition site and an SD sequence of ldh at its 5'-terminal side. The primer of SEQ ID NO: 44 has a KpnI recognition site at its 5'-terminal side.

The genomic DNA of *L. lactis* subsp. *lactis* ATCC 19435 was isolated. PCR was carried out under usual conditions, using the isolated genomic DNA as a template and using the oligonucleotide primers of SEQ ID NO: 43 and 44. The amplified DNA fragment was purified, and digested with XbaI. The digested fragment was mixed with a fragment obtained by digesting the pBRgapP obtained in Example 8 with restriction enzymes XbaI and PshAI, and the fragments were ligated using a ligase. Thereafter, a competent cell of *Escherichia coli* DH5α strain (trade name: DNA-903, Toyobo Co., Ltd.)) was transformed with the ligation product, and a transformant that grew on an LB agar plate containing 50 µg/mL ampicillin was obtained. The obtained colony was cultured in an LB liquid medium containing 50 µg/mL ampicillin overnight at 37° C. A plasmid containing lctO was obtained from the resultant bacterial cells and was named "pGAP-lctO".

The base sequence of the isolated lctO was determined using a DNA sequencer.

Example 12

<Construction of Plasmid for Producing Lactic Acid>

The pGAP-cscA obtained in Example 8 was cleaved with restriction enzymes KpnI and SalI, and purified, thereby providing a purified fragment. PCR was carried out in a manner similar to Example 9, using ATGGTACCCG-GAGAAAGTCTTATGGAAAAAACATAT-CAAGCAGGTACAAATG (SEQ ID NO: 45) and CAGTC-GACTTAAATAAAACGATTCTCACGCAATTTTA (SEQ ID NO: 46) as primers, as a result of which a lox fragment was obtained. PCR was carried out in a manner similar to Example 10 using ATGGTACCCGGAGAAAGTCTTAT-GATTATTTCCGCAGCCAGCGATTATCG (SEQ ID NO: 27) and GATGTCGACCTATGCCGCATTC-CCTTTCGCCATG (SEQ ID NO: 28) as primers, as a result of which a lldD fragment was obtained. PCR was carried out in a manner similar to Example 11 using AATGGTACCCG-GAGAAAGTCTTATGCATCTATCATCTA-CAGATGTAAACTTTA (SEQ ID NO: 47) and ACAGTC-GACTTAGTCAATCAATGAGGTATGTTTGATTT (SEQ ID NO: 48) as primers, as a result of which a lctO fragment was obtained. Each of the fragments obtained above was cleaved with restriction enzymes KpnI and SalI. Each fragment was mixed with the fragment of pGAP-cscA obtained above, and the fragments were ligated using a ligase. Thereafter, competent cells of *Escherichia coli* DH5α strain (trade name: DNA-903, Toyobo Co. Ltd.)) were respectively transformed with the ligation products, and transformants that grew on an LB agar plate containing 50 µg/mL ampicillin were obtained. From the transformants obtained, spGAP-cscA-lox, pGAP-cscA-lldD, and pGAP-cscA-lctO were obtained. Further, PCR was carried out using the genomic DNA of *Escherichia coli* as a template, and using ATCGTC-GACCGGAGAAAGTCTTATGATTATTTC-CGCAGCCAGCGATTATCG (SEQ ID NO: 42) and GAT-GTCGACCTATGCCGCATTCCCTTTCGCCATG (SEQ ID NO: 28) as primers, as a result of which a lldD fragment was obtained. The fragment was then cleaved with a restriction enzyme SalI, and purified. The purified fragment was mixed with a fragment obtained by digesting the pGAP-cscA-lox with a restriction enzyme SalI, and the fragments were ligated using a ligase. Thereafter, a competent cell of *Escherichia coli* DH5α strain (trade name: DNA-903, Toyobo Co., Ltd.)) was transformed with the ligation product, and a transformant that grew on an LB agar plate containing 50 µg/mL ampicillin was obtained. From the transformant obtained, a plasmid pGAP-cscA-lox-lldD was obtained. The insertion direction was confirmed by sequencing. Further, PCR was carried out using the genomic DNA of *Escherichia coli* as a template, and using ATCGTCGACCGGAGAAAGTCTTATGAT-TATTTCCGCAGCCAGCGATTATCG (SEQ ID NO: 42) and GATGTCGACCTATGCCGCATTCCCTTTCGCCATG (SEQ ID NO: 28) as primers, as a result of which an lldD fragment was obtained. The lldD fragment was then cleaved with a restriction enzyme SalI, and purified. The purified fragment was mixed with a fragment obtained by cleaving the pGAP-cscA-lctO with a restriction enzyme SalI, and the fragments were ligated using a ligase. Thereafter, a competent cell of *Escherichia coli* DH5α strain (trade name: DNA-903, Toyobo Co., Ltd.)) was transformed with the ligation product, and a transformant that grew on an LB agar plate containing 50 µg/mL ampicillin was obtained. A plasmid pGAP-cscA-lctO-lldD was obtained from the obtained transformant. These plasmids were individually used to transform the MG1655ΔpflΔdldΔmdhΔaspΔfruR/GAPldhA genome-inserted variant obtained in Example 7, as a result of which a pGAP-cscA-lox/MG1655ΔpflΔdldΔmdhΔaspΔfruR/GA-PldhA genome-inserted variant, a pGAP-cscA-lldD/ MG1655ΔpflΔdldΔmdhΔaspΔfruR/GAPldhA genome-inserted variant, a pGAP-cscA-lctO/ MG1655ΔpflΔdldΔmdhΔaspΔfruR/GAPldhA genome-inserted variant, a pGAP-cscA-lox-lldD/ MG1655ΔpflΔdldΔmdhΔaspΔfruR/GAPldhA genome-inserted variant, and a pGAP-cscA-lctO-lldD/ MG1655ΔpflΔdldΔmdhΔaspΔfruR/GAPldhA genome-inserted variant, were obtained.

Example 13

<Effects of LldD Enhancement>

The MG1655ΔpflΔdldΔmdhΔasp/GAPldhA genome-inserted variant prepared in Example 6 was transformed with the plasmids pBRgapP and pGAP-lldD, as a result of which a pBRgapP/MG1655ΔpflΔdldΔmdhΔasp/GAPldhA genome-inserted variant and a pGAP-lldD/ MG1655ΔpflΔdldΔmdhΔasp/GAPldhA genome-inserted variant were obtained.

As preculture, 100 mL of an LB medium (Difco cat. 244620) containing ampicillin at a concentration of 50 µg/mL was placed in 500mL-volume Erlenmeyer flasks equipped with baffles, the D-lactic acid-producing bacteria described above were separately seeded thereto, and were cultured overnight at 35° C. with stirring at 120 rpm. Thereafter, the resultant precultures were separately seeded, at 0.5%, into 1

L-volume culture vessels (trade name: BMJ-01, culture apparatus manufactured by ABLE Corporation), each of which contained 500 mL of a medium (12% glucose, 3% corn steep liquor: manufactured by Nihon Shokuhin Kako Co., Ltd., Lot(190718C), the same shall apply hereinafter). Cultivation was carried out for 48 hours at atmospheric pressure with an aeration rate of 0.5 vvm, a stirring speed of 200 rpm, a culture temperature of 35° C., and a pH of 7.2. Assay of lactic acid in the resultant culture liquid was carried out by HPLC according to a conventional method. The optical purity of the lactic acid generated was calculated according to the following equation from the amount of L-lactic acid and amount of D-lactic acid in the resultant supernatant as measured using an F-Kit D-/L-lactic acid (Product code: 1112821, J.K. International Inc.).

Optical purity (% e.e.)=100×(D-lactic acid concentration−L-lactic acid concentration)/(D-lactic acid concentration+L-lactic acid concentration)

The results are given in Table 1. As shown in Table 1, it was demonstrated that enhancement of lldD improves the optical purity of lactic acid obtained.

a culture temperature of 35° C., and a pH of 7.5. Assay of lactic acid in the resultant culture liquid was carried out by HPLC according to an conventional method. The optical purity of the lactic acid generated was calculated according to the following equation from the amount of L-lactic acid and the amount of D-lactic acid in the resultant supernatant as measured using an F-Kit D-/L-lactic acid (Product code: 1112821, J.K. International Inc.).

Optical purity (% e.e.)=100×(D-lactic acid concentration−L-lactic acid concentration)/(D-lactic acid concentration+L-lactic acid concentration)

For comparison, the above-prepared pGAP-lldD/MG1655ΔpflΔdldΔmdhΔasp/GAPldhA genome-inserted variant before introduction of mutation was cultured in the same manner.

TABLE 1

| | Variant | |
|---|---|---|
| | pBRgapP/MG1655ΔpflΔdldΔmdhΔasp/GAPldhA genome-inserted variant | pGAP-lldD/MG1655ΔpflΔdldΔmdhΔasp/GAPldhA genome-inserted variant |
| Lactic acid concentration (g/L) | 99.8 | 97.9 |
| Optical purity (% e.e.) | 99.2 | 100 |

<Effects of LldD Enhancement by Mutated lldD>

The MG1655ΔpflΔdldΔmdhΔasp/GAPldhA genome-inserted variant prepared in Example 6 was transformed with the pGAP-mutated lldD obtained in Example 10, as a result of The results are shown in Table 2. As shown in Table 2, it was demonstrated that the use of mutated lldD improves the optical purity of lactic acid obtained, as compared to lldD before introduction of mutation.

TABLE 2

| | Variant | |
|---|---|---|
| | pGAP-lldD/MG1655ΔpflΔdldΔmdhΔasp/GAPldhA genome-inserted variant | pGAP-mutated lldD/MG1655ΔpflΔdldΔmdhΔasp/GAPldhA genome-inserted variant |
| Lactic acid concentration (g/L) | 94.4 | 87.9 |
| Optical purity (% e.e.) | 97.8 | 98.3 | which a pGAP-mutated lldD/MG1655ΔpflΔdldΔmdhΔasp/GAPldhA genome-inserted variant was obtained. As preculture, 100 mL of an LB medium (Difco cat. 244620) containing ampicillin at a concentration of 50 µg/mL was placed in a 500 mL-volume Erlenmeyer flasks equipped with baffles, the D-lactic acid-producing bacteria described above were separately seeded thereto, and were cultured overnight at 35° C. with stirring at 120 rpm. Thereafter, the resultant precultures were separately seeded, at 0.5%, into a 1 L-volume culture vessels (trade name: BMJ-01, culture apparatus manufactured by ABLE Corporation), each of which contained 500 mL of a medium (12% glucose, 5% corn steep liquor). Cultivation was carried out for 30 hours at atmospheric pressure with an aeration rate of 0.5 vvm, a stirring speed of 200 rpm, <Effects of lldR Disruption>

The MG1655ΔpflΔdldΔmdhΔaspΔlldR/GAPldhA genome-inserted variant, which is the lldR-disrupted variant obtained in Example 6, was transformed with the pGAP-lldD obtained in Example 10. As preculture for the resultant colony, 100 mL of an LB medium (Difco cat. 244620) containing ampicillin at a concentration of 50 µg/mL was placed in 500 mL-volume Erlenmeyer flasks equipped with baffles, and the D-lactic acid-producing bacteria described above were seeded thereto, and were cultured overnight at 35° C. with stirring at 120 rpm. Thereafter, the resultant precultures were separately seeded, at 0.5%, into a 1 L-volume culture vessels (trade name: BMJ-01, culture apparatus manufactured by ABLE Corporation) each of which contained 500 mL of a medium (12% glucose, 5% corn steep liquor). Cultivation was carried out for 30 hours at atmospheric pressure with an aeration rate of 0.5 vvm, a stirring speed of 200 rpm, a culture temperature of 35° C., and a pH of 7.5. Assay of the lactic acid concentration in the resultant culture liquid was measured by HPLC according to a conventional method. The optical purity of the lactic acid generated was calculated according to the following equation from the amount of L-lactic acid and the amount of D-lactic acid in the resultant supernatant as measured using an F-Kit D-/L-lactic acid (Product code: 1112821, J.K. International Inc.).

Optical purity (% e.e.)=100×(D-lactic acid concentration−L-lactic acid concentration)/(D-lactic acid concentration+L-lactic acid concentration)

For comparison, the pGAP-lldD/MG1655ΔpflΔdldΔmdhΔasp/GAPldhA genome-inserted variant before in which lldR was not disrupted was cultured in the same manner.

The results are given in Table 3. As shown in Table 3, it was demonstrated that disruption of lldR improves the optical purity of lactic acid obtained, as compared to before the disruption of lldR.

contained 500 mL of a medium (12% glucose, 5% corn steep liquor). Cultivation was carried out for 24 hours at atmospheric pressure with an aeration rate of 0.5 vvm, a stirring speed of 200 rpm, a culture temperature of 35° C., and a pH of 7.4. Assay of the lactic acid concentration in the resultant culture liquid was carried out by HPLC according to a conventional method. The optical purity of the lactic acid generated was calculated according to the following equation from the amount of L-lactic acid and the amount of D-lactic acid in the resultant supernatant as measured using an F-Kit D-/L-lactic acid (Product code: 1112821, J.K. International Inc.).

Optical purity (% e.e.)=100×(D-lactic acid concentration−L-lactic acid concentration)/(D-lactic acid concentration+L-lactic acid concentration)

For comparison, the pGAP-mutated lldD/MG1655ΔpflΔdldΔmdhΔaspΔlldR/GAPldhA genome-inserted variant, which is the mutated lldD-enhanced variant obtained above, was cultured in the same manner. The results

TABLE 3

| | Variant | |
|---|---|---|
| | pGAP-lldD/MG1655ΔpflΔdldΔmdhΔasp/GAPldhA genome-inserted variant | pGAP-lldD/MG1655ΔpflΔdldΔmdhΔaspΔlldR/GAPldhA genome-inserted variant |
| Lactic acid concentration (g/L) | 96.2 | 94.4 |
| Optical purity (% e.e.) | 97.6 | 98.2 |

<Effects of Lox Enhancement>

Cells of the MG1655ΔpflΔdldΔmdhΔaspΔlldR/GAPldhA genome-inserted variant, which is the lldR-disrupted variant obtained in Example 6, were respectively transformed with the pGAP-lox obtained in Example 9 and the pGAP-lox-mutated lldD obtained in Example 10. As preculture for the are shown in Table 4. As shown in Table 4, it was demonstrated that enhancement of Lox has an effect in terms of improving the optical purity, which is stronger than that achieved by enhancement by the lldD gene variant. It was demonstrated that co-enhancement of Lox and mutated lldD improves the optical purity of lactic acid obtained.

TABLE 4

| | Variant | | |
|---|---|---|---|
| | pGAP-mutated lldD/MG1655ΔpflΔdldΔmdhΔaspΔlldR/GAPldhA genome-inserted variant | pGAP-lox/MG1655ΔpflΔdldΔmdhΔaspΔlldR/GAPldhA genome-inserted variant | pGAP-lox-mutated lldD/MG1655ΔpflΔdldΔmdhΔaspΔlldR/GAPldhA genome-inserted variant |
| Lactic acid concentration (g/L) | 79.3 | 72.8 | 67.3 |
| Optical purity (% e.e.) | 97.1 | 98.7 | 99.2 | resultant colonies, 100 mL of an LB medium (Difco cat. 244620) containing ampicillin at a concentration of 50 μg/mL was placed in 500 mL Erlenmeyer flasks equipped with baffles, and the D-lactic acid-producing bacteria described above were separately seeded thereto, and were cultured overnight at 35° C. with stirring at 120 rpm. Thereafter, the resultant precultures were separately seeded, at 0.5%, into 1 L-volume culture vessels (trade name: BMJ-01, culture apparatus manufactured by ABLE Corporation) each of which <Production of D-Lactic Acid from Molasses>

As preculture, the pGAP-cscA-lldD/MG1655ΔpflΔdldΔmdhΔaspΔfruR/GAPldhA genome-inserted variant and the pGAP-cscA-lox-lldD/MG1655ΔpflΔdldΔmdhΔaspΔfruR/GAPldhA genome-inserted variant obtained in Example 12 were separately seeded into 100 mL-volume Erlenmeyer flasks equipped with baffles, each of which contained 20 mL of the preculture liquid shown in Table 5, and cultivation was carried out overnight at 35° C. with stirring at 120 rpm. Thereafter, the resultant precultures were separately seeded, at 0.5%, into 1 L-volume culture vessels (trade name: BMJ-01, culture apparatus manufactured by ABLE Corporation), each of which contained 500 mL of the medium shown in Table 6. Cultivation was carried out for 48 hours at atmospheric pressure with an aeration rate of 0.5 vvm, a stirring speed of 350 rpm, a culture temperature of 35° C., and a pH of 7.5. The concentration of lactic acid in the resultant culture liquid was measured by HPLC according to a conventional method. The optical purity of lactic acid generated was calculated according to the following equation from the amount of L-lactic acid and the amount of D-lactic acid in the resultant supernatant as measured using an F-Kit D-/L-lactic acid (Product code: 1112821, J.K. International Inc.).

Optical purity (% e.e.)=100×(D-lactic acid concentration−L-lactic acid concentration)/(D-lactic acid concentration+L-lactic acid concentration)

TABLE 5

| Preculture medium composition | |
| --- | --- |
| Molasses (inedible, manufactured by Dai-Nippon Meiji Sugar Co., Ltd.) | 2% |
| Corn steep liquor (manufactured by Nihon Shokuhin Kako Co., Ltd.) | 10% |
| Water | Balance | pH 7.8 after autoclaving (adjusted by 24% NaOH)

TABLE 6

| Medium composition | |
| --- | --- |
| Molasses (inedible, manufactured by Dai-Nippon Meiji Sugar Co., Ltd.) | 20% |
| Corn steep liquor (manufactured by Nihon Shokuhin Kako Co., Ltd.) | 5% |
| Water | Balance | pH 7.5 after autoclaving (adjusted by 24% NaOH)

For comparison, a pGAP-cscA/MG1655ΔpflΔdldΔmdhΔaspΔfruR/GAPldhA genome-inserted variant in which the pGAP-cscA obtained in Example 8 was recombined into the MG1655ΔpflΔdldΔmdhΔaspΔfruR/GAPldhA genome-inserted variant obtained in Example 7 was cultured in the same manner.

The results are shown in Table 7. As shown in Table 7, it was demonstrated that the optical purity of lactic acid obtained is improved by enhancement of LldD and Lox, also when molasses is used as a raw material.

<Effects of LctO Enhancement>

As preculture, the pGAP-cscA-lldD/MG1655ΔpflΔdldΔmdhΔaspΔfruR/GAPldhA genome-inserted variant and the pGAP-cscA-lctO-lldD/MG1655ΔpflΔdldΔmdhΔaspΔfruR/GAPldhA genome-inserted variant obtained in Example 12 were separately seeded into 100 mL-volume Erlenmeyer flasks equipped with baffles, to which 10 g of calcium carbonate (first grade, Junsei Chemical Co., Ltd.) was added and sterilized in advance, and to which 20 mL of the medium shown in Table 8 was further added, and the variants were cultured overnight at 35° C. with stirring at 120 rpm. The preculture liquids were added, in an amount of 1 mL, to 100 mL Erlenmeyer flasks equipped with baffles, to which 10 g of calcium carbonate (first grade, Junsei Chemical Co., Ltd.) was added and sterilized in advance, and to which 20 mL of the medium shown in Table 8 was further added. Cultivation was carried out for 24 hours at 35° C. with stirring at 100 rpm.

TABLE 8

| Medium composition | |
| --- | --- |
| Molasses (inedible, manufactured by Dai-Nippon Meiji Sugar Co., Ltd.) | 20% |
| Corn steep liquor (manufactured by Nihon Shokuhin Kako Co., Ltd.) | 5% |
| Water | Balance | pH 8.0 after autoclaving (adjusted by 24% NaOH)

After the cultivation was completed, lactic acid in the resultant culture liquid was assayed by HPLC according to a conventional method. The optical purity of the lactic acid generated was calculated according to the following equation from the amount of L-lactic acid and the amount of D-lactic acid in the resultant supernatant as measured using an F-Kit D-/L-lactic acid (Product code: 1112821, J.K. International Inc.).

Optical purity (% e.e.)=100×(D-lactic acid concentration−L-lactic acid concentration)/(D-lactic acid concentration +L-lactic acid concentration)

The results are given in Table 9. As shown in Table 9, it was demonstrated that enhancement of lctO improves the optical purity of lactic acid obtained.

TABLE 7

| | Variant | | |
| --- | --- | --- | --- |
| | pGAP-cscA/MG1655ΔpflΔdld ΔmdhΔaspΔfruR/GAPldhA genome-inserted variant | pGAP-cscA-lldD/MG1655ΔpflΔdld ΔmdhΔaspΔfruR/GAPldhA genome-inserted variant | pGAP-cscA-lox-lldD/MG1655Δpfl ΔdldΔmdhΔaspΔfruR/GAPldhA genome-inserted variant |
| Lactic acid concentration (g/L) | 94.7 | 100.9 | 95.7 |
| Optical purity (% e.e.) | 97.8 | 98.3 | 100 |

TABLE 9

| | Variant | |
|---|---|---|
| | pGAP-cscA-lldD/MG1655ΔpflΔdldΔmdh ΔaspΔfruR/GAPldhA genome-inserted variant | pGAP-cscA-lctO-lldD/MG1655ΔpflΔdldΔmdh ΔaspΔfruR/GAPldhA genome-inserted variant |
| Lactic acid concentration (g/L) | 57.4 | 54.5 |
| Optical purity (% e.e.) | 98.3 | 99.6 |

—L-Lactic Acid-producing Bacterium—

Example 14

<Construction of Expression Vector for *Bifidobacterium*-derived ldh2 Gene and Preparation of Transformant MG1655Δpfl/pGAP-ldh2 Variant with the Expression Vector>

The amino acid sequence of NAD-dependent L-lactate dehydrogenase of *Bifidobacterium longum* and the base sequence of the gene thereof have already been reported. That is, the NAD-dependent L-lactate dehydrogenase-encoding gene (ldh2) is described at 555 to 1517 of the *Bifidobacterium* genome sequence at GenBank accession number M33585.

The promoter sequence of *Escherichia coli*-derived glyceraldehyde-3-phosphate dehydrogenase (hereinafter also referred to as "GAPDH") that is described at 397-440 in the base sequence information of GenBank accession number X02662 may be used as the base sequence of a promoter necessary for the expressing the gene.

In order to obtain the GAPDH promoter, amplification by a PCR method was carried out using the genomic DNA of *Escherichia coli* MG1655 strain as a template and using CGAGCTACATATGCAATGATTGACACGATTCCG (SEQ ID NO: 33) and TCTAGAGCTATTTGTTAGTGAATAAAAGG (SEQ ID NO: 34). The resultant DNA fragment was digested with a restriction enzyme NdeI, thereby providing a DNA fragment of about 110 by corresponding to the GAPDH promoter. The resultant DNA fragment was mixed with a fragment obtained by digesting a plasmid pBR322 (GenBank accession number J01749) with restriction enzymes NdeI and PvuII, and the fragments were ligated using a ligase. Thereafter, a competent cell of an *Escherichia coli* DH5α strain (trade name: DNA-903, Toyobo Co., Ltd.)) was transformed with the ligation product, and a transformant that grew on an LB agar plate containing 50 µg/mL ampicillin was obtained. The obtained colony was cultured in an LB liquid medium containing 50 µg/mL ampicillin overnight at 37° C., and a plasmid pBRgapP was recovered from the resultant bacterial cells.

In order to obtain an NAD-dependent L-lactate dehydrogenase gene, amplification by a PCR method was carried out by using *Bifidobacterium longum* (ATCC 15707) as a template and using AATCTAGACGGAGAAAGTCTTATGGCGGAAACTACCGTTAAGC (SEQ ID NO: 49) and CTGTCTAGATCAGAAGCCGAACTGGGCG (SEQ ID NO: 50). The resultant DNA fragment was digested with a restriction enzyme XbaI, thereby providing an L-lactate dehydrogenase gene fragment of about 1.0 kbp. The resultant DNA fragment was mixed with a fragment obtained by digesting the plasmid pBRgapP constructed above with a restriction enzyme XbaI, and the fragments were ligated using a ligase. Thereafter, a competent cell of *Escherichia coli* DH5α strain (trade name: DNA-903, Toyobo Co., Ltd.)) was transformed with the ligation product, and a transformant that grew on an LB agar plate containing 50 µg/mL ampicillin was obtained. The obtained colony was cultured in an LB liquid medium containing 50 µg/mL ampicillin overnight at 37° C., and a plasmid pGAP-ldh2 was recovered from the resultant bacterial cells.

A competent cell of MG1655 strain of which the pfl gene had been deleted in a manner similar to that employed in Example 2 by using the pTHΔpfl constructed in Example 3 (referred to as "MG1655Δpfl variant") was transformed with the plasmid pGAP-ldh2, and the obtained transformant was cultured on an Miller's LB Broth agar plate containing 50 µg/mL ampicillin overnight at 37° C., thereby providing an MG1655Δpfl/pGAP-ldh2 variant.

Example 15

<Production of L-Lactic Acid by MG1655Δpfl/pGAP-ldh2 Variant>

Similarly to Example 13, production of L-lactic acid from glucose by the MG1655Δpfl/pGAP-ldh2 variant was examined.

25 mL of the flask contents obtained by preculturing in a manner similar to Example 13 was seeded into 475 g of the medium shown in Table 10 below.

TABLE 10

| Glucose | 12% |
|---|---|
| Yeast extract (manufactured by Difco Laboratories Inc.) | 3% |
| Water | Balance |

Cultivation was carried out for 18 hours at atmospheric pressure with an aeration rate of 0.25 L/min, a stirring speed of 200 rpm, a culture temperature of 35° C., and a pH of 7.5 (adjusted with 24% NaOH).

After cultivation for 18 hours, the concentration of L-lactic acid in the culture liquid was 97.02 g/L.

From these results, it was confirmed that L-lactic acid can be produced from glucose by using the *Bifidobacterium*-derived NAD-dependent L-lactate dehydrogenase.

Example 16

<Preparation of MG1655ΔpflΔdldΔmdhΔasp/GAPldhA Genome-inserted Variant/pGAP-ldh2 Variant>

A transformant was prepared by introducing the pGAP-ldh2 plasmid constructed in Example 14 into the D-lactic acid-producing variant prepared in Example 6. Specifically, the following procedure was adopted.

A competent cell of MG1655ΔpflΔdldΔmdhΔasp/GAPldhA genome-inserted variant prepared in Example 6 was transformed with the plasmid pGAP-ldh2. The obtained transformant was cultured on an Miller's LB Broth agar plate containing 50 µg/mL ampicillin overnight at 37° C., thereby providing an MG1655ΔpflΔdldΔmdhΔasp/GAPldhA genome-inserted variant/pGAP-ldh2 variant.

Example 17

<Production of L-Lactic Acid by MG1655ΔpflΔdldΔmdhΔasp/GAPldhA Genome-inserted Variant/pGAP-ldh2 Variant>

Similarly to Example 13, production of L-lactic acid from glucose by the MG1655ΔpflΔdldΔmdhΔasp/GAPldhA genome-inserted variant/pGAP-ldh2 variant was examined.

Cultivation was carried out for 18 hours at atomospheric pressure with an aeration rate of 0.25 L/min, a stirring speed of 200 rpm, a culture temperature of 35° C., and a pH of 7.5 (adjusted with 24% NaOH).

After cultivation for 18 hours, the concentration of L-lactic acid in the culture liquid was 116.84 g/L.

From these results, it was confirmed that L-lactic acid can be produced from glucose as a raw material by integrating the plasmid pGAP-ldh2 into a D-lactic acid-producing *Escherichia coli* variant. The production of L-lactic acid was confirmed by measuring the amount of L-lactic acid and the amount of D-lactic acid by using a F-Kit D-/L-lactic acid (Product code: 1112821, J.K. International Inc.).

Example 18

<Preparation of MG1655ΔpflΔmdhΔaspΔlldDΔldhA/GAPldh2 Genome-inserted Variant>

The ldh2 gene was substituted for the ldhA gene of the *Escherichia coli* variant for production of D-lactic acid used in Example 15, and lldD, which is the gene of an enzyme that catalyzes the decomposition of L-lactic acid, was disrupted, thereby preparing an *Escherichia coli* variant for production of L-lactic acid (MG1655ΔpflΔdldΔmdhΔasp/GAPldhA genome-inserted variant). Specifically, the following procedure was adopted.

(Preparation of ldhA Gene-Disrupted Variant)

Based on the gene information of regions of *Escherichia coli* MG1655 genomic DNA adjacent to the ldhA gene, four kinds of oligonucleotide primer, AAGGTACCACCA-GAGCGTTCTCAAGC (SEQ ID NO: 21), GCTCTAGAT-TCTCCAGTGATGTTGAATCAC (SEQ ID NO: 22), GCTCTAGAGCATTCCTGACAGCAGAAGC (SEQ ID NO: 51), and AACTGCAGTCGGCGTGTAGTAGTGAACC (SEQ ID NO: 52), were synthesized. Using these primers, a plasmid pTHΔldhA for gene disruption was constructed in a manner similar to Example 1. Further, a competent cell of MG1655ΔpflΔdldΔmdhΔasp/GAPldhA genome-inserted variant was transformed with the pTHΔldhA, and an ldhA-deleted variant was selected in a manner similar to Example 2. The resultant variant was named "MG1655ΔpflΔdldΔmdhΔasp/GAPldhA genome-inserted ΔldhA variant".

(Preparation of dld Gene Revertant)

Based on the gene information of regions of *Escherichia coli* MG1655 genomic DNA adjacent to the dld gene, two kinds of oligonucleotide primer, CAACAC-CAAGCTTTCGCG (SEQ ID NO: 1) and TGTTCTA-GAAAGTTCTTTGAC (SEQ ID NO: 4), were synthesized. PCR was carried out using these primers and using the genomic DNA of *Escherichia coli* MG1655 as a template, and the resultant DNA fragment was cleaved with restriction enzymes HindIII and XbaI. Further, a plasmid pTH18cs1 was cleaved with restriction enzymes HindIII and XbaI, mixed with the dld fragment, and the fragments were then ligated using a ligase, thereby constructing a plasmid pTHDLD.

Further, a competent cell of MG1655ΔpflΔdldΔmdhΔasp/GAPldhA genome-inserted variant was transformed with the pTHDLD, and a dld revertant was selected in a manner similar to Example 2. The resultant variant was named "MG1655ΔpflΔmdhΔasp/GAPldhA genome-inserted ΔldhA variant".

(Preparation of lldD Gene-disrupted Variant)

Based on the gene information of regions of MG1655 strain genomic DNA adjacent to the lldD gene, four kinds of oligonucleotide primer, GGAAGCTTCAAATTG-GCGTCTCTGATCT (SEQ ID NO: 53), AAACCCGGGC-CATCCATATAGTGGAACAGGAACGG (SEQ ID NO: 54), GGGCTCGAGTGGCGATGACGCTGACTGG (SEQ ID NO: 55) and CGTCTAGAACGGGTAAATCTGGTGGT-GACCGTCACCCG (SEQ ID NO: 56), were synthesized. Using these primers, a plasmid pTHΔlldD for gene disruption was constructed in a manner similar to Example 1. Further, a competent cell of MG1655ΔpflΔmdhΔasp/GAPldhA genome-inserted ΔldhA variant was transformed with the pTHΔlldD, and an lldD-deleted variant was selected in a manner similar to Example 2. The resultant variant was named "MG1655ΔpflΔmdhΔaspΔlldD/GAPldhA genome-inserted ΔldhA variant".

(Preparation of ldh2 Gene Genome-inserted Variant)

The amino acid sequence of NAD-dependent L-lactate dehydrogenase of *Bifidobacterium longum* and the base sequence of the gene thereof have already been reported. That is, the NAD-dependent L-lactate dehydrogenase-encoding gene (ldh2) is described at 555 to 1517 of the *Bifidobacterium* genome sequence at GenBank accession number M33585.

In order to obtain the gene (ldh2) encoding L-lactate dehydrogenase, two kinds of oligonucleotide primer, AAGAAT-TCCGGAGAAAGTCTTATGGCGGAAAC-TACCGTTAAGC (SEQ ID NO: 57) and CTGTCTAGATCAGAAGCCGAACTGGGCG (SEQ ID NO: 50), were synthesized using the genomic DNA of *Bifidobacterium longum* (ATCC15707) as a template. PCR was carried out using these primers, and the resultant DNA fragment was cleaved with restriction enzymes EcoRI and XbaI.

In order to obtain the GAPDH promoter, two kinds of oligonucleotide primer, GGTCTAGAGCAATGATTGA-CACGATTCCG (SEQ ID NO: 58) and CGGAATTCCGC-TATTTGTTAGTGAATAAAAG (SEQ ID NO: 59), were synthesized using the genomic DNA of *Escherichia coli* MG1655 strain as a template. The resultant DNA fragment was cleaved with restriction enzymes EcoRI and XbaI.

A plasmid obtained by cleaving the pTHΔldhA obtained in Example 15 with XbaI, the EcoRI-XbaI fragment of *Bifidobacterium longum*-derived ldh2 obtained as described above, and the EcoRI-XbaI fragment of *Escherichia coli*-derived GAPDH promoter were mixed, and the fragments were ligated using a ligase. Thereafter, a competent cell of *Escherichia coli* DH5α strain (trade name: DNA-903, Toyobo Co., Ltd.)) was transformed with the ligation product, and a transformant that grew on an LB agar plate containing 50 μg/mL ampicillin was obtained. The obtained colony was cultured in an LB liquid medium containing 50 μg/mL ampicillin overnight at 37° C., and a plasmid pTHΔldhA::GAPldh2 was recovered from the resultant bacterial cells. An MG1655ΔpflΔmdhΔaspΔlldD/GAPldhA genome-inserted ΔldhA variant was transformed with the obtained plasmid, and an ldh2 genome-inserted variant was selected, by PCR amplification of ldh2, in a manner similar to Example 2.

The variant obtained was named "MG1655ΔpflΔmdhΔaspΔlldDΔldhA/GAPldh2 genome-inserted variant".

Example 19

<Preparation of MG1655ΔpflΔmdhΔaspΔlldDΔldhA/GAPldh2 Genome-inserted/pGAP-cscA Variant>

An expression vector for a sucrose hydrolase (invertase) gene was introduced into the *Escherichia coli* variant for production of L-lactic acid prepared in Example 16, thereby providing an *Escherichia coli* variant that produces L-lactic acid from sucrose. Specifically, the following procedure was adopted.

A competent cell of MG1655ΔpflΔmdhΔaspΔlldDΔldhA/GAPldh2 genome-inserted variant prepared in Example 16 was transformed with the plasmid pGAP-cscA constructed in Example 8, and the obtained transformant was cultured on an Miller's LB Broth agar plate containing 50 μg/mL ampicillin overnight at 37° C., as a result of which an MG1655ΔpflΔmdhΔaspΔlldDΔldhA/GAPldh2 genome-inserted/pGAP-cscA variant was obtained.

Example 20

<Preparation of *Escherichia coli* Expressing *Escherichia coli*-derived FAD-Dependent D-Lactate Dehydrogenase>

Based on the gene information of regions of MG1655 strain genomic DNA adjacent to the did gene, two kinds of oligonucleotide primer, CGGGTACCTTCGCCACCA-CAAGGAGTGGA (SEQ ID NO: 60), GGTCTAGAGTC-GACTTACTCCACTTCCTGCCAGTT (SEQ ID NO: 61), were synthesized. PCR was carried out using these primers, and the resultant DNA fragment was cleaved with restriction enzymes KpnI and SalI. This fragment was mixed with a fragment obtained by cleaving the pGAP-cscA constructed in Example 8 with KpnI and SalI, and the fragments were ligated using a ligase. Thereafter, a competent cell of *Escherichia coli* DH5α strain (trade name: DNA-903, Toyobo Co., Ltd.)) was transformed with the ligation product, and a transformant that grew on an LB agar plate containing 50 μg/mL ampicillin was obtained. The obtained colony was cultured in an LB liquid medium containing 50 μg/mL ampicillin overnight at 37° C., and a plasmid pGAP-cscA-dld(EC) was recovered from the resultant bacterial cells.

Example 21

<Preparation of *Escherichia coli* Expressing *Corynebacterium glutamicum*-derived FAD-dependent D-Lactate Dehydrogenase>

The amino acid sequence of *Corynebacterium glutamicum*-derived FAD-dependent D-lactate dehydrogenase, and the base sequence of the gene thereof are described at 261009 to 259294 of the *Corynebacterium glutamicum* genome sequence at GenBank accession number BX927150.

In order to obtain the FAD-dependent D-lactate dehydrogenase-encoding gene (dld), two kinds of oligonucleotide primer, GCGGTACCCGGAGAAAGTCTTATGACG-CAACCAGGACAG (SEQ ID NO: 62) and TGGGTACCT-TAGGCCCAGTCCTTGTGCGGCGACGTGC (SEQ ID NO: 63), were synthesized using the genomic DNA of *Corynebacterium glutamicum* (NBRC12168) as a template. *Corynebacterium glutamicum* (NBRC12168) is available from NITE Biological Resource Center. PCR was carried out using these primers, and the resultant DNA fragment was cleaved with a restriction enzyme KpnI. This fragment was mixed with a fragment obtained by cleaving the pGAP-cscA constructed in Example 8 with KpnI, and the fragments were ligated using a ligase. Thereafter, a competent cell of *Escherichia coli* DH5α strain (trade name: DNA-903, Toyobo Co., Ltd.)) was transformed with the ligation product, and a transformant that grew on an LB agar plate containing 50 μg/mL ampicillin was obtained. The obtained colony was cultured in an LB liquid medium containing 50 μg/mL ampicillin overnight at 37° C., and a plasmid pGAP-cscA-dld(CG) was recovered from the resultant bacterial cells.

Example 22

<Preparation of *Escherichia coli* Expressing *Zymomonas mobilis*-derived FAD-Dependent D-Lactate Dehydrogenase>

The amino acid sequence of *Zymomonas mobilis*-derived FAD-dependent D-lactate dehydrogenase and the base sequence of the gene thereof are described at 256658 to 258382 of the *Zymomonas mobilis* genome sequence at GenBank accession number AE008692.

In order to obtain the FAD-dependent D-lactate dehydrogenase-encoding gene (dld), two kinds of oligonucleotide primer, GCGGTACCCGGAGAAAGTCTTATGGTG-CAGCTTCCTTC (SEQ ID NO: 64) and GTGGTAC-CCTATCTCCAATAAGCGGCCTTGCTGGTATG (SEQ ID NO: 65), were synthesized, and PCR was carried out using the primers and using the genomic DNA of *Zymomonas mobilis* (ATCC 31821) as a template. The resultant DNA fragment was cleaved with a restriction enzyme KpnI. This fragment was mixed with a fragment obtained by cleaving the pGAP-cscA constructed in Example 8 with KpnI, and the fragments were ligated using a ligase. Thereafter, a competent cell of *Escherichia coli* DH5α strain (trade name: DNA-903, Toyobo Co., Ltd.)) was transformed with the ligation product, and a transformant that grew on an LB agar plate containing 50 μg/mL ampicillin was obtained. The obtained colony was cultured in an LB liquid medium containing 50 μg/mL ampicillin overnight at 37° C., and a plasmid pGAP-cscA-dld (ZM) was recovered from the resultant bacterial cells.

Example 23

<Preparation of *Escherichia coli* Expressing *Xanthomonas campestris*-derived FAD-Dependent D-Lactate Dehydrogenase>

The amino acid sequence of *Xanthomonas campestris*-derived FAD-dependent D-lactate dehydrogenase and the base sequence of the gene thereof are described at 10284 to 8890 of *Xanthomonas campestris* genome sequence at GenBank accession number AE012169.

In order to obtain the FAD-dependent D-lactate dehydrogenase-encoding gene (dld), two kinds of oligonucleotide primer, AACCCGGGCGGAGAAAGTCTTATGACT-GATGGACTTCCCACCGC (SEQ ID NO: 66) and ATC-CCGGGTCACTCTGCGGGCGAT-
GTGGGCAGCACCTTGCCCGGATTC (SEQ ID NO: 67), were synthesized, and PCR was carried out using the primers and using the genomic DNA of *Xanthomonas campestris* (ATCC 33913) as a template. The resultant DNA fragment was cleaved with a restriction enzyme SmaI. This fragment was mixed with a fragment obtained by cleaving the pGAP-cscA constructed in Example 8 with KpnI and blunting the restriction enzyme cleavage sites by using a DNA Blunting Kit (TAKARA Cat. 6025), and the fragments were ligated using a ligase. Thereafter, a competent cell of *Escherichia coli* DH5α strain (trade name: DNA-903, Toyobo Co., Ltd.)) was transformed with the ligation product, and a transformant that grew on an LB agar plate containing 50 μg/mL ampicillin was obtained. The obtained colony was cultured in an LB liquid medium containing 50 μg/mL ampicillin overnight at 37° C., and a plasmid pGAP-cscA-dld(XC) was recovered from the resultant bacterial cells.

Example 24

<Preparation of *Escherichia coli* Expressing *Xanthomonas oryzae*-derived FAD-dependent D-Lactate Dehydrogenase>

The amino acid sequence of *Xanthomonas oryzae*-derived FAD-dependent D-lactate dehydrogenase and the base sequence of the gene thereof are described at 4098235 to 4099662 of *Xanthomonas oryzae* genome sequence at GenBank accession number AE013598.

In order to obtain the FAD-dependent D-lactate dehydrogenase-encoding gene (dld), two kinds of oligonucleotide primer, TTGGTACCGGAGAAAGTCTTATGAC-CGATGTACTTCCCACCGCAC (SEQ ID NO: 68) and TTGGTACCTAGGCGGGCGGCAACACCT-TGCCAGGATTCAAGATCCCA (SEQ ID NO: 69), were synthesized using the genomic DNA of *Xanthomonas oryzae* (JCM 20241) as a template, and PCR was carried out using them. The resultant DNA fragment was cleaved with a restriction enzyme KpnI. This fragment was mixed with a fragment obtained by cleaving the pGAP-cscA constructed in Example 8 with KpnI, and the fragments were ligated using a ligase. Thereafter, a competent cell of *Escherichia coli* DH5α strain (trade name: DNA-903, Toyobo Co., Ltd.)) was transformed with the ligation product, and a transformant that grew on an LB agar plate containing 50 μg/mL ampicillin was obtained. The obtained colony was cultured in an LB liquid medium containing 50 μg/mL ampicillin overnight at 37° C., and a plasmid pGAP-cscA-dld(XO) was recovered from the resultant bacterial cells.

JCM 20241 is available from Japan Collection of Microorganisms.

Example 25

<Optical Purity of L-Lactic Acid Produced by *Escherichia coli* Expressing FAD-dependent D-Lactate Dehydrogenase with or without Membrane Binding Domain of D-Lactate Dehydrogenase>

The MG1655ΔpflΔmdhΔaspΔlldDΔfruRΔldhA/GAPldh2 genome-inserted variant prepared in Example 18 was transformed with each of the following plasmids, thereby providing *Escherichia coli* variants that express FAD-dependent D-lactate dehydrogenases of which the origins are different from one another.

(A): pGAP-cscA obtained in Example 8
(B): pGAP-cscA-dld(EC) obtained in Example 20
(C): pGAP-cscA-dld(CG) obtained in Example 21
(D): pGAP-cscA-dld(ZM) obtained in Example 22
(E): pGAP-cscA-dld(XC) obtained in Example 23
(F): pGAP-cscA-dld(XO) obtained in Example 24

As preculture, the FAD-dependent D-lactate dehydrogenase-expressing variants were respectively seeded into 100 mL-volume Erlenmeyer flasks equipped with baffles, each of which contained 20 mL of the preculture liquid shown in Table 11, and cultivation was carried out overnight at 35° C. with stirring at 120 rpm. Thereafter, the preculture liquids were respectively added, in an amount of 1 mL, to 100 mL-volume Erlenmeyer flasks equipped with baffles, to which 10 g of calcium carbonate (first grade, Junsei Chemical Co., Ltd.) had been added and sterilized in advance, and to which 20 mL of the medium shown in Table 12 had been further added. Cultivation was carried out for 24 hours overnight at 35° C. with stirring at 100 rpm.

TABLE 11

| Preculture liquid composition | |
|---|---|
| Molasses (inedible, manufactured by Dai-Nippon Meiji Sugar Co., Ltd.) | 2% |
| Corn steep liquor (manufactured by Nihon Shokuhin Kako Co., Ltd.) | 10% |
| Water | Balance | pH 7.8 After autoclaving (adjusted by 24% NaOH)

TABLE 12

| Medium composition | |
|---|---|
| Molasses (inedible, manufactured by Dai-Nippon Meiji Sugar Co., Ltd.) | 20% |
| Corn steep liquor (manufactured by Nihon Shokuhin Kako Co., Ltd.) | 5% |
| Water | Balance | pH 8.0 after autoclaving (adjusted by 24% NaOH)

After the cultivation was completed, the supernatant was obtained by centrifugation. The optical purity was calculated according to the following equation from the amount of L-lactic acid and the amount of D-lactic acid in the resultant supernatant as measured using an F-Kit D-/L-lactic acid (Product code: 1112821, J.K. International Inc.).

Optical purity (% e.e.)=100×(L-lactic acid concentration−D-lactic acid concentration)/(L-lactic acid concentration+D-lactic acid concentration)

The results are given in Table 13. As shown in Table 13, it was demonstrated that an *Escherichia coli* expressing the *Escherichia coli*-derived, *Corynebacterium glutamicum*-derived, or *Zymomonas mobilis*-derived dld, each of which has a Lact-deh-memb domain, achieves particularly high optical purity within a short time.

TABLE 13

| Origin of FAD-dependent D-lactate dehydrogenase | Plasmid | Domain | | | Optical purity (% e.e.) |
| | | FAD binding domain | Lact-deh-memb | FAD-oxidase_C | |
|---|---|---|---|---|---|
| Control | (A) | — | — | — | 96.1 |
| *Escherichia coli* | (B) | Present | Present | Absent | 98.7 |
| *Corynebacterium glutamicum* | (C) | Present | Present | Present | 99.8 |
| *Zymomonas mobilis* | (D) | Present | Present | Present | 99.9 |
| *Xanthomonas campestris* | (E) | Present | Absent | Present | 96.4 |
| *Xanthomonas oryzae* | (F) | Present | Absent | Present | 96.4 |

Disclosures of Japanese Patent Application No. 2008-237177 filed on Sep. 16, 2008, Japanese Patent Application No. 2009-32042 filed on Feb. 13, 2009, and Japanese Patent Application No. 2009-32043 filed on Feb. 13, 2009 are incorporated herein by reference in their entirety.

All publications, patent applications, and technical standards mentioned in this specification are herein incorporated by reference to the same extent as if each individual publication, patent application, or technical standard was specifically and individually indicated to be incorporated by reference.

The invention claimed is:

1. A lactic acid-producing *Escherichia coli* comprising
   an enzymatic activity of a NAD-dependent lactate dehydrogenase which is enhanced so as to produce D-lactic acid and an enzymatic activity of a NAD-independent lactate oxidoreductase, which is enhanced so as to decompose L-lactic acid, or
   an enzymatic activity of an NAD-dependent lactate dehydrogenase which is enhanced so as to produce L-lactic acid and an enzymatic activity of a NAD-independent lactate oxidoreductase which is enhanced so as to decompose D-lactic acid.

2. The lactic acid-producing *Escherichia coli* according to claim 1, wherein the enhancement of the NAD-dependent lactate dehydrogenase activity causes production of one of D-lactic acid or L-lactic acid from pyruvic acid, and the enhancement of the NAD-independent lactate oxidoreductase activity causes decomposition of the other one of D-lactic acid or L-lactic acid as a substrate.

3. The lactic acid-producing *Escherichia coli* according to claim 2, wherein the enhancement of the NAD-dependent lactate dehydrogenase activity is enhancement of D-lactate dehydrogenase (LdhA) activity, and provides capability of producing D-lactic acid.

4. The lactic acid-producing *Escherichia coli* according to claim 3, wherein the enhancement of the NAD-independent lactate oxidoreductase activity is enhancement of NAD-independent L-lactate dehydrogenase (LldD) activity, enhancement of L-lactate oxidase activity, inactivation or attenuation of LldR, or a combination of one or more thereof, and provides capability of producing D-lactic acid.

5. The lactic acid-producing *Escherichia coli* according to claim 4, wherein the L-lactate oxidase is at least one of Lox or LctO.

6. The lactic acid-producing *Escherichia coli* according to claim 4, wherein the enhancement of the NAD-independent lactate oxidoreductase activity is by a mutated lldD gene having a silent mutation at position 33 in ORF of a LldD-encoding gene, wherein the mutated lldD is represented by a base sequence of SEQ ID NO: 41.

7. The lactic acid-producing *Escherichia coli* according to claim 3, wherein at least one selected from the group consisting of FAD-dependent D-lactate dehydrogenase (Dld) activity and pyruvate formate lyase (Pfl) activity is inactivated or attenuated.

8. The lactic acid-producing *Escherichia coli* according to claim 2, wherein the enhancement of the NAD-dependent lactate dehydrogenase activity is enhancement of NAD-dependent L-lactate dehydrogenase activity, and provides capability of producing L-lactic acid.

9. The lactic acid-producing *Escherichia coli* according to claim 8, wherein the enhancement of the NAD-independent lactate oxidoreductase activity is enhancement of activity of Dld, and provides capability of producing L-lactic acid.

10. The lactic acid-producing *Escherichia coli* according to claim 8, wherein the L-lactate dehydrogenase is obtained from a bacterium of the genus *Bifidobacterium*.

11. The lactic acid-producing *Escherichia coli* according to claim 9, wherein the Dld comprises a Lact deh memb domain.

12. The lactic acid-producing *Escherichia coli* according to claim 9, wherein the Dld is derived from at least one selected from the group consisting of *Escherichia coli*, *Zymomonas* and *Corynebacterium*.

13. The lactic acid-producing *Escherichia coli* according to claim 8, wherein at least one of LdhA activity, LldD activity or Pfl activity is inactivated or attenuated.

14. The lactic acid-producing *Escherichia coli* according to claim 1, wherein at least one selected from the group consisting of malate dehydrogenase (Mdh) activity and aspartate ammonia lyase (AspA) activity is inactivated or attenuated.

15. The lactic acid-producing *Escherichia coli* according to claim 1, wherein at least one selected from the group consisting of sucrose non-PTS genes and fructose-1-phosphate kinase (FruK) is enhanced.

16. The lactic acid-producing *Escherichia coli* according to claim 1, wherein FruR activity is inactivated or attenuated.

17. A method of producing lactic acid, the method comprising:
    producing lactic acid by using the lactic acid-producing *Escherichia coli* of claim 1.

18. A method of producing D-lactic acid, the method comprising:
    producing D-lactic acid by using the lactic acid-producing *Escherichia coli* of claim 3.

19. A method of producing L-lactic acid, the method comprising:
    producing L-lactic acid by using the lactic acid-producing *Escherichia coli* of claim 8.

* * * * *